US012594141B2

(12) United States Patent
McIntyre et al.

(10) Patent No.: US 12,594,141 B2
(45) Date of Patent: Apr. 7, 2026

(54) SYSTEMS, METHODS, AND MEDIA FOR PRESENTING BIOPHYSICAL SIMULATIONS IN AN INTERACTIVE MIXED REALITY ENVIRONMENT

(71) Applicant: Case Western Reserve University, Cleveland, OH (US)

(72) Inventors: Cameron McIntyre, Cleveland, OH (US); Angela Noecker, Cleveland, OH (US); Jeffrey Mlakar, Cleveland, OH (US); Mark Griswold, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 18/566,463

(22) PCT Filed: Jun. 3, 2022

(86) PCT No.: PCT/US2022/032189
§ 371 (c)(1),
(2) Date: Dec. 1, 2023

(87) PCT Pub. No.: WO2022/256670
PCT Pub. Date: Dec. 8, 2022

(65) Prior Publication Data
US 2024/0261057 A1     Aug. 8, 2024

Related U.S. Application Data

(60) Provisional application No. 63/263,082, filed on Oct. 26, 2021, provisional application No. 63/202,274, filed on Jun. 3, 2021.

(51) Int. Cl.
*G06F 3/01*          (2006.01)
*A61B 5/00*         (2006.01)
(Continued)

(52) U.S. Cl.
CPC ............ *A61B 90/37* (2016.02); *A61B 5/0042* (2013.01); *A61B 5/055* (2013.01); *A61B 34/10* (2016.02);
(Continued)

(58) Field of Classification Search
CPC ....... A61B 90/37; A61B 5/0042; A61B 5/055; A61B 34/10; A61B 2034/102;
(Continued)

(56) References Cited

U.S. PATENT DOCUMENTS

| | | | |
|---|---|---|---|
| 9,278,208 B1 * | 3/2016 | Gilson | A61N 1/36067 |
| 11,775,052 B1 * | 10/2023 | Douglas | G06F 3/0346 |
| | | | 600/431 |

(Continued)

FOREIGN PATENT DOCUMENTS

WO          2014155203 A1    10/2014

OTHER PUBLICATIONS

Setsompop, Kawin, et al. "Pushing the limits of in vivo diffusion MRI for the Human Connectome Project." Neuroimage 80 (2013): 220-233.
(Continued)

*Primary Examiner* — Sanghyuk Park
(74) *Attorney, Agent, or Firm* — Quarles & Brady LLP

(57) ABSTRACT

Systems, methods, and media for presenting biophysical simulations in an interactive mixed reality environment are provided. In some embodiments, a system comprises: a head mounted display comprising: a transparent display; sensors; and a processor programmed to: receive medical imaging data associated with a subject; receive, from a server, information useable to visualize a simulation of biophysical processes and a subject-specific anatomical model based on the medical imaging data; cause a visualization of the simulation to be presented, via the transparent display, in
(Continued)

connection with the medical imaging data and an instrument in a first position; receive, from the server, updated information useable to visualize an updated simulation with the instrument in a second position; and cause a visualization of the updated simulation to be presented with the instrument presented in the second position.

20 Claims, 16 Drawing Sheets

(51) Int. Cl.
| | |
|---|---|
| *A61B 5/055* | (2006.01) |
| *A61B 34/10* | (2016.01) |
| *A61B 90/00* | (2016.01) |
| *G16H 30/20* | (2018.01) |

(52) U.S. Cl.
CPC .............. *G06F 3/011* (2013.01); *G06F 3/017* (2013.01); *G16H 30/20* (2018.01); *A61B 2034/102* (2016.02); *A61B 2034/105* (2016.02); *A61B 2090/365* (2016.02)

(58) Field of Classification Search
CPC ........ A61B 2034/104; A61B 2034/105; A61B 2034/107; A61B 2034/2048; A61B 2034/2074; A61B 2017/00203; A61B 2017/00207; A61B 2017/00216; A61B 2090/365; A61B 2090/372; A61B 2090/374; A61B 2090/502; G06F 3/011; G06F 3/017; G16H 30/20; A61N 1/0534; G02B 27/017; A61G 90/361

See application file for complete search history.

(56) References Cited

U.S. PATENT DOCUMENTS

| | | | |
|---|---|---|---|
| 2008/0114233 A1 | 5/2008 | McIntyre et al. | |
| 2012/0093381 A1 | 4/2012 | Fan et al. | |
| 2013/0046230 A1 | 2/2013 | Lewis, Jr. et al. | |
| 2015/0087963 A1 | 3/2015 | Tyc et al. | |
| 2017/0367771 A1* | 12/2017 | Tako ..................... | G06T 19/003 |
| 2018/0235704 A1 | 8/2018 | Gonzalez-Martinez et al. | |
| 2019/0108638 A1* | 4/2019 | Zagorchev ......... | G01R 33/5608 |
| 2019/0223779 A1* | 7/2019 | Mersmann ........... | A61B 5/4094 |
| 2019/0282324 A1* | 9/2019 | Freeman .............. | A61H 31/005 |
| 2020/0038119 A1 | 2/2020 | Geri et al. | |
| 2020/0302694 A1* | 9/2020 | Flexman ............... | G06V 20/20 |
| 2021/0260280 A1* | 8/2021 | Gordon ............. | A61M 39/0247 |
| 2022/0272272 A1* | 8/2022 | Keenan ................ | H04N 23/959 |

OTHER PUBLICATIONS

Starr, Philip A. "Placement of deep brain stimulators into the subthalamic nucleus or globus pallidus internus: technical approach." Stereotactic and functional neurosurgery 79.3-4 (2003): 118-145.

Thomas, Cibu, et al. "Anatomical accuracy of brain connections derived from diffusion MRI tractography is inherently limited." Proceedings of the National Academy of Sciences 111.46 (2014): 16574-16579.

Van Essen, David C., and Matthew F. Glasser. "Parcellating cerebral cortex: how invasive animal studies inform noninvasive mapmaking in humans." Neuron 99.4 (2018): 640-663.

Van Essen, David C., et al. "The WU-Minn human connectome project: an overview." Neuroimage 80 (2013): 62-79.

Welter, Marie-Laure, et al. "Optimal target localization for subthalamic stimulation in patients with Parkinson disease." Neurology 82.15 (2014): 1352-1361.

Wish-Baratz, Susanne, et al. "A new supplement to gross anatomy dissection: HoloAnatomy." Medical education 53.5 (2019): 522-523.

Yeh, Fang-Cheng, et al. "Population—averaged atlas of the macroscale human structural connectome and its network topology." Neuroimage 178 (2018): 57-68.

Yu, Chunxiu, et al. "Frequency-specific optogenetic deep brain stimulation of subthalamic nucleus improves parkinsonian motor behaviors." Journal of Neuroscience 40.22 (2020): 4323-4334.

International Search Report in PCT/US2022/032189.

Abosch, Aviva, et al. "An international survey of deep brain stimulation procedural steps." Stereotactic and functional neurosurgery 91.1 (2013): 1-11.

Agrawal, Abhishek, et al. "Josef Klingler's models of white matter tracts: influences on neuroanatomy, neurosurgery, and neuroimaging." Neurosurgery 69.2 (2011): 238-254.

Archer, Derek B., David E. Vaillancourt, and Stephen A. Coombes. "A template and probabilistic atlas of the human sensorimotor tracts using diffusion MRI." Cerebral cortex 28.5 (2018): 1685-1699.

Avants, Brian B., et al. "The Insight ToolKit image registration framework." Frontiers in neuroinformatics 8 (2014): 44.

Basser, Peter J., James Mattiello, and Denis LeBihan. "MR diffusion tensor spectroscopy and imaging." Biophysical journal 66.1 (1994): 259-267.

Coenen, Volker Arnd, et al. "One-pass deep brain stimulation of dentato-rubro-thalamic tract and subthalamic nucleus for tremor-dominant or equivalent type Parkinson's disease." Acta Neurochirurgica 158 (2016): 773-781.

Coude, Dymka, Andre Parent, and Martin Parent. "Single-axon tracing of the corticosubthalamic hyperdirect pathway in primates." Brain Structure and Function 223 (2018): 3959-3973.

De Roquemaurel, Alexis, et al. "Stimulation Sweet Spot in Subthalamic Deep Brain Stimulation—Myth or Reality? A Critical Review of Literature." Stereotactic and Functional Neurosurgery 99.5 (2021): 425-442.

Duchin, Yuval, et al. "Patient-specific anatomical model for deep brain stimulation based on 7 Tesla MRI." PloS one 13.8 (2018): e0201469.

Essayed, Walid I., et al. "White matter tractography for neurosurgical planning: A topography-based review of the current state of the art." NeuroImage: Clinical 15 (2017): 659-672.

Fischl, Bruce. "FreeSurfer." Neuroimage 62.2 (2012): 774-781.

Frankemolle, Anneke MM, et al. "Reversing cognitive-motor impairments in Parkinson's disease patients using a computational modelling approach to deep brain stimulation programming." Brain 133.3 (2010): 746-761.

Gallay, Marc N., et al. "Human pallidothalamic and cerebellothalamic tracts: anatomical basis for functional stereotactic neurosurgery." Brain Structure and Function 212 (2008): 443-463.

Gradinaru, Viviana, et al. "Optical deconstruction of parkinsonian neural circuitry." science 324.5925 (2009): 354-359.

Gunalan, Kabilar, Bryan Howell, and Cameron C. McIntyre. "Quantifying axonal responses in patient-specific models of subthalamic deep brain stimulation." Neuroimage 172 (2018): 263-277.

Hamel, Wolfgang, et al. "Targeting of the subthalamic nucleus for deep brain stimulation: a survey among Parkinson disease specialists." World neurosurgery 99 (2017): 41-46.

Haynes, William IA, and Suzanne N. Haber. "The organization of prefrontal-subthalamic inputs in primates provides an anatomical substrate for both functional specificity and integration: implications for Basal Ganglia models and deep brain stimulation." Journal of Neuroscience 33.11 (2013): 4804-4814.

Horn, Andreas, et al. "Lead-DBS v2: Towards a comprehensive pipeline for deep brain stimulation imaging." Neuroimage 184 (2019): 293-316.

Howell, Bryan, Kabilar Gunalan, and Cameron C. McIntyre. "A driving-force predictor for estimating pathway activation in patient-specific models of deep brain stimulation." Neuromodulation: Technology at the Neural Interface 22.4 (2019): 403-415.

Ivan, Michael E., et al. "Brain shift during bur hole-based procedures using interventional MRI." Journal of neurosurgery 121.1 (2014): 149-160.

Jones, Derek K., Thomas R. Knosche, and Robert Turner. "White matter integrity, fiber count, and other fallacies: the do's and don'ts of diffusion MRI." Neuroimage 73 (2013): 239-254.

(56) References Cited

OTHER PUBLICATIONS

Juhnke, Bethany, et al. "Extended Reality Tools for Deep Brain Stimulation: A Framework and Design Concepts for Procedural Planning." Frontiers in Biomedical Devices. vol. 83549. American Society of Mechanical Engineers, 2020.

Kim, Jinyoung, et al. "Automatic localization of the subthalamic nucleus on patient-specific clinical MRI by incorporating 7 T MRI and machine learning: Application in deep brain stimulation." Human brain mapping 40.2 (2019): 679-698.

Klein, Arno, et al. "Evaluation of 14 nonlinear deformation algorithms applied to human brain MRI registration." Neuroimage 46.3 (2009): 786-802.

Krack, Paul, et al. "Deep brain stimulation in movement disorders: from experimental surgery to evidence-based therapy." Movement Disorders 34.12 (2019): 1795-1810.

Lehman, Julia F., et al. "Rules ventral prefrontal cortical axons use to reach their targets: implications for diffusion tensor imaging tractography and deep brain stimulation for psychiatric illness." Journal of Neuroscience 31.28 (2011): 10392-10402.

RJ, Macuiunas. "The application accuracy of stereotactic frames." Neurosurgery 35 (1994): 682-695.

Maier-Hein, Klaus H., et al. "The challenge of mapping the human connectome based on diffusion tractography." Nature communications 8.1 (2017): 1349.

Maks, Christopher B., et al. "Deep brain stimulation activation volumes and their association with neurophysiological mapping and therapeutic outcomes." Journal of Neurology, Neurosurgery & Psychiatry 80.6 (2009): 659-666.

Meola, Antonio, et al. "Augmented reality in neurosurgery: a systematic review." Neurosurgical review 40 (2017): 537-548.

Meola, Antonio, et al. "Human connectome-based tractographic atlas of the brainstem connections and surgical approaches." Neurosurgery 79.3 (2016): 437-455.

Miocinovic, Svjetlana, et al. "Computational analysis of subthalamic nucleus and lenticular fasciculus activation during therapeutic deep brain stimulation." Journal of neurophysiology 96.3 (2006): 1569-1580.

Morecraft, R. J., et al. "Localization of orofacial representation in the corona radiata, internal capsule and cerebral peduncle in Macaca mulatta." Journal of Comparative Neurology 525.16 (2017): 3429-3457.

Mori, Susumu, et al. "Three-dimensional tracking of axonal projections in the brain by magnetic resonance imaging." Annals of Neurology: Official Journal of the American Neurological Association and the Child Neurology Society 45.2 (1999): 265-269.

Noecker, Angela M., et al. "StimVision software: examples and applications in subcallosal cingulate deep brain stimulation for depression." Neuromodulation: Technology at the Neural Interface 21.2 (2018): 191-196.

Noecker, Angela M., et al. "StimVision v2: Examples and applications in subthalamic deep brain stimulation for Parkinson's disease." Neuromodulation: Technology at the Neural Interface 24.2 (2021): 248-258.

Nowacki, Andreas, et al. "Accuracy of different three-dimensional subcortical human brain atlases for DBS—lead localisation." NeuroImage: Clinical 20 (2018): 868-874.

Patenaude, Brian, et al. "A Bayesian model of shape and appearance for subcortical brain segmentation." Neuroimage 56.3 (2011): 907-922.

Pauli, Wolfgang M., Amanda N. Nili, and J. Michael Tyszka. "A high-resolution probabilistic in vivo atlas of human subcortical brain nuclei." Scientific data 5.1 (2018): 1-13.

Petersen, Mikkel V., et al. "Holographic reconstruction of axonal pathways in the human brain." Neuron 104.6 (2019): 1056-1064.

Plaha, Puneet, et al. "Stimulation of the caudal zona incerta is superior to stimulation of the subthalamic nucleus in improving contralateral parkinsonism." Brain 129.7 (2006): 1732-1747.

Plantinga, Birgit R., et al. "Individualized parcellation of the subthalamic nucleus in patients with Parkinson's disease with 7T MRI." Neuroimage 168 (2018): 403-411.

Riva-Posse, Patricio, et al. "A connectomic approach for subcallosal cingulate deep brain stimulation surgery: prospective targeting in treatment-resistant depression." Molecular psychiatry 23.4 (2018): 843-849.

Rolston, John D., et al. "An unexpectedly high rate of revisions and removals in deep brain stimulation surgery: analysis of multiple databases." Parkinsonism & related disorders 33 (2016): 72-77.

Safadi, Ziad, et al. "Functional segmentation of the anterior limb of the internal capsule: linking white matter abnormalities to specific connections." Journal of Neuroscience 38.8 (2018): 2106-2117.

Sammartino, Francesco, and Mojgan Hodaie. "Diffusion tensor imaging of the basal ganglia for functional neurosurgery applications." Current Concepts in Movement Disorder Management 33 (2018): 62-79.

Sato, Fumi, et al. "Single-axon tracing study of neurons of the external segment of the globus pallidus in primate." Journal of Comparative Neurology 417.1 (2000): 17-31.

Sato, Fumi, et al. "Axonal branching pattern of neurons of the subthalamic nucleus in primates." Journal of Comparative Neurology 424.1 (2000): 142-152.

Schilling, Kurt G., et al. "Limits to anatomical accuracy of diffusion tractography using modern approaches." Neuroimage 185 (2019): 1-11.

Schmitz, Daniel, et al. "Derivation of fiber orientations from oblique views through human brain sections in 3D-polarized light imaging." Frontiers in neuroanatomy 12 (2018): 75.

* cited by examiner

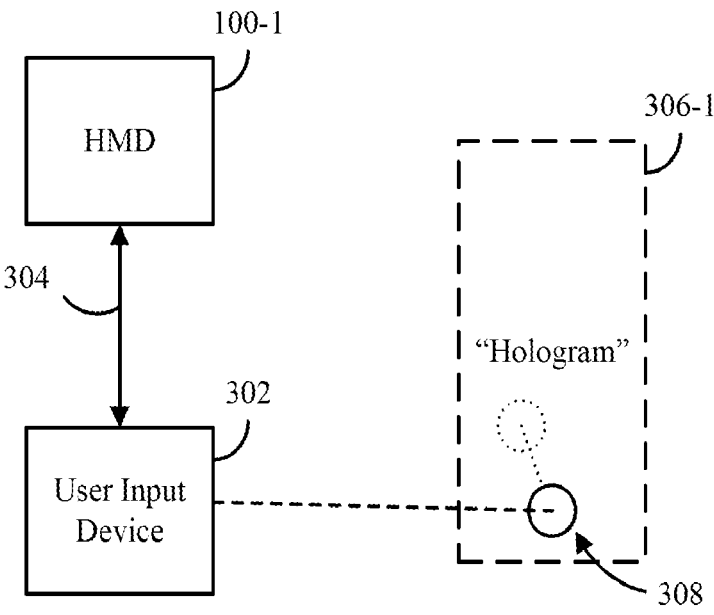
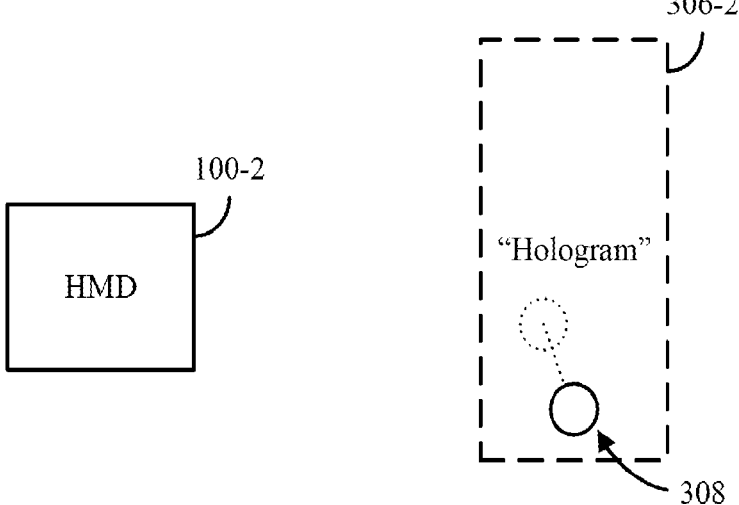
FIG. 3A

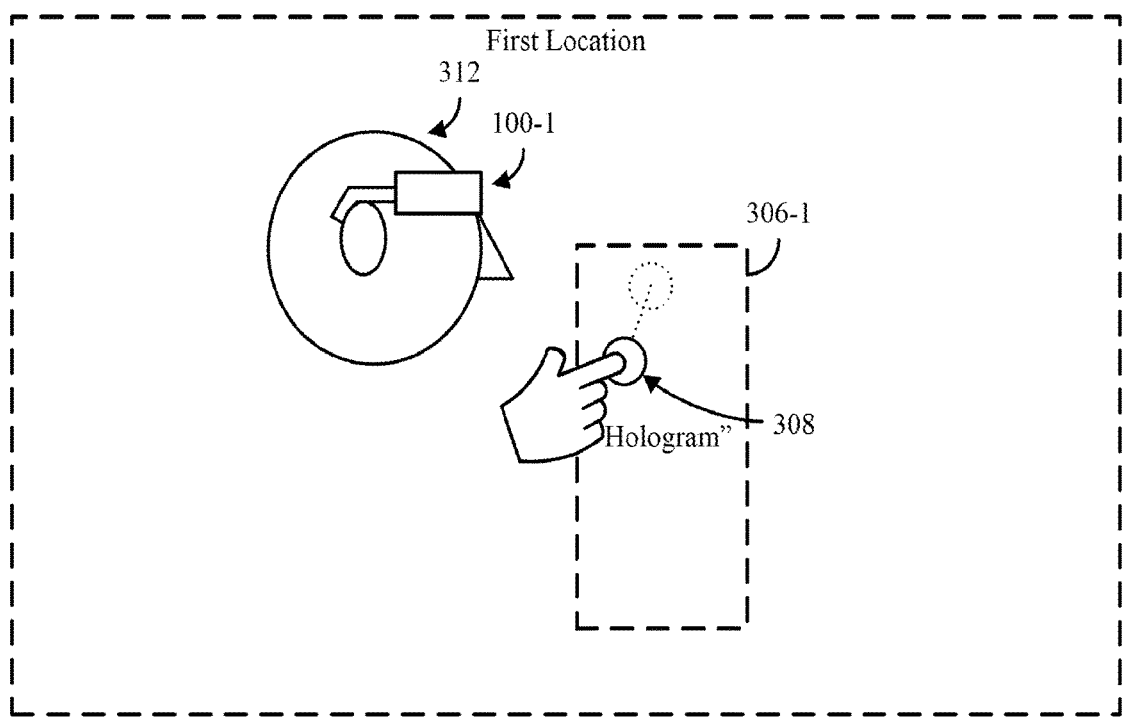
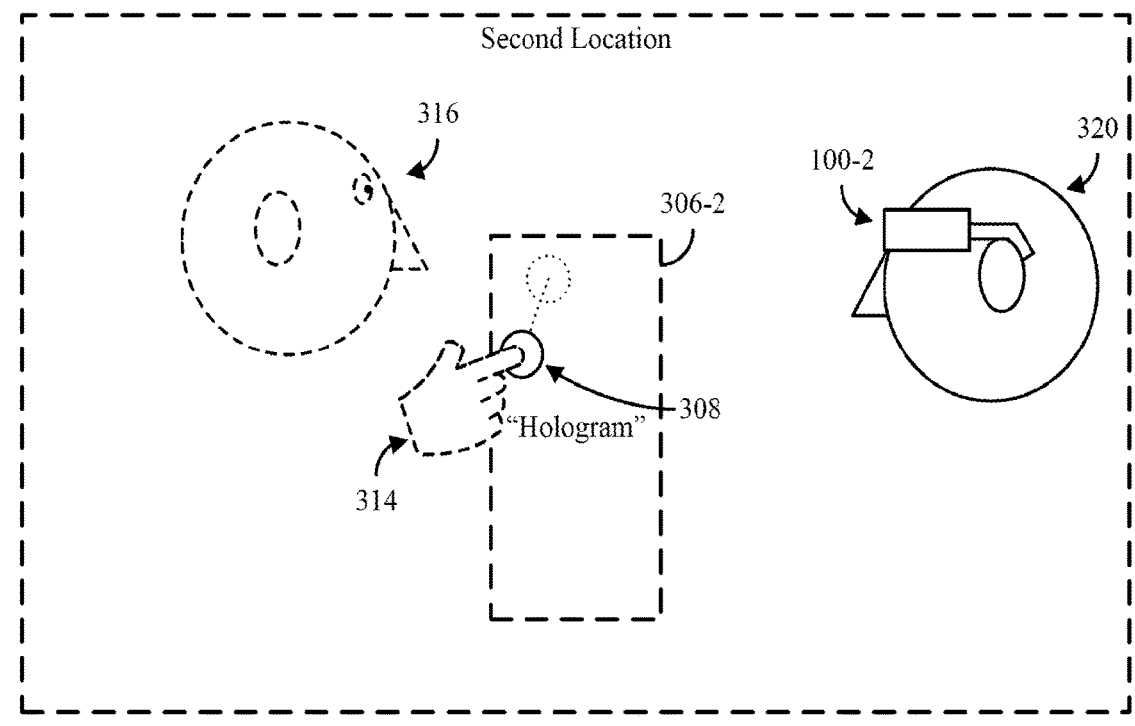
FIG. 3B

600

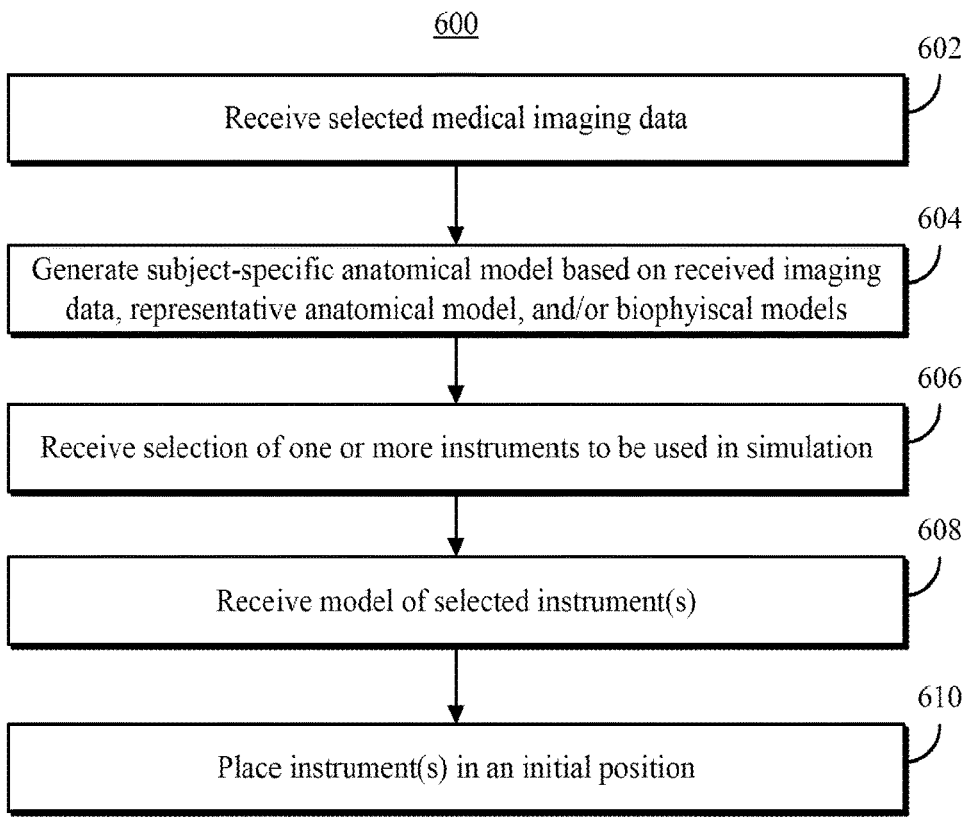

602
Receive selected medical imaging data

604
Generate subject-specific anatomical model based on received imaging data, representative anatomical model, and/or biophyiscal models 606
Receive selection of one or more instruments to be used in simulation 608
Receive model of selected instrument(s)

610
Place instrument(s) in an initial position

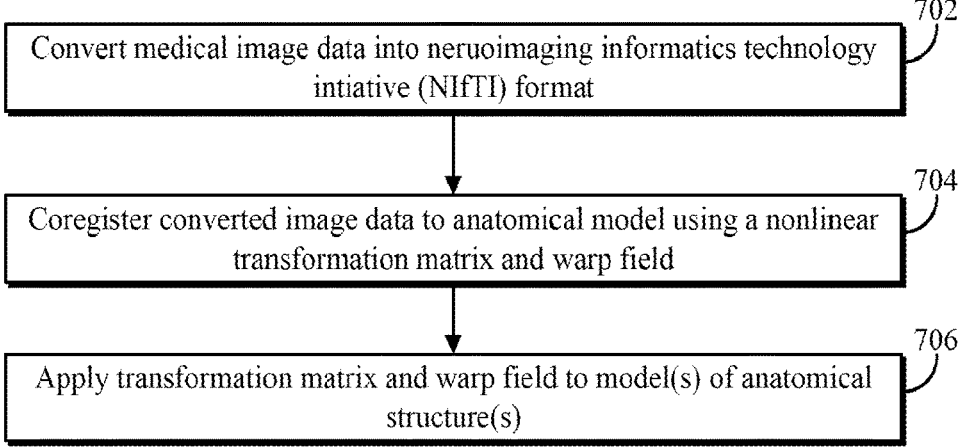

702
Convert medical image data into neruoimaging informatics technology intiative (NIfTI) format 704
Coregister converted image data to anatomical model using a nonlinear transformation matrix and warp field 706
Apply transformation matrix and warp field to model(s) of anatomical structure(s)

FIG. 7

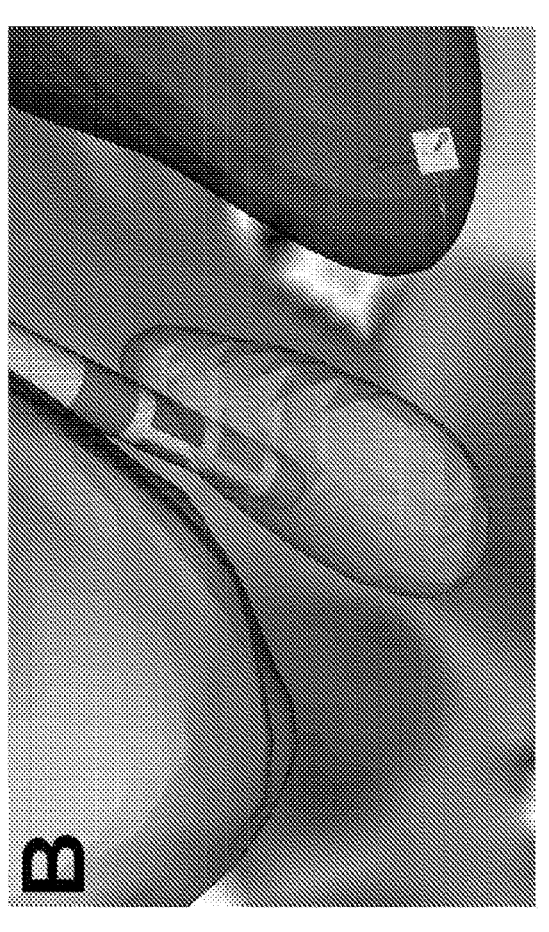
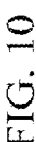
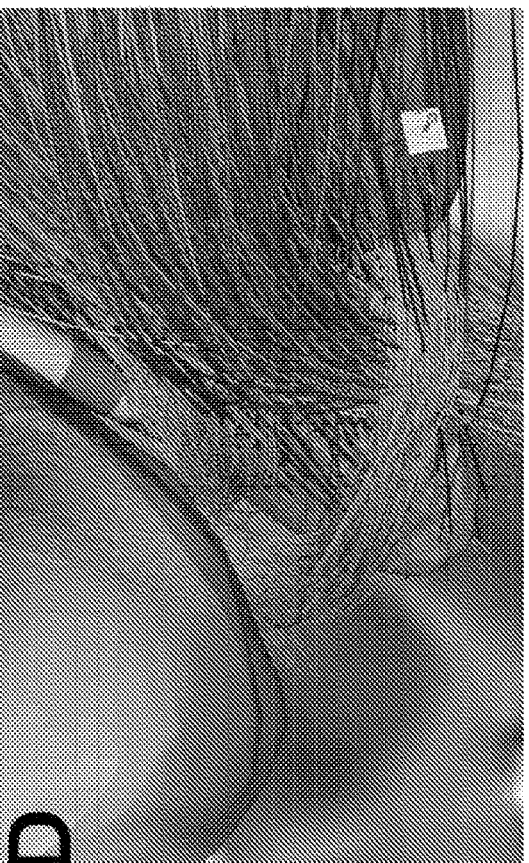
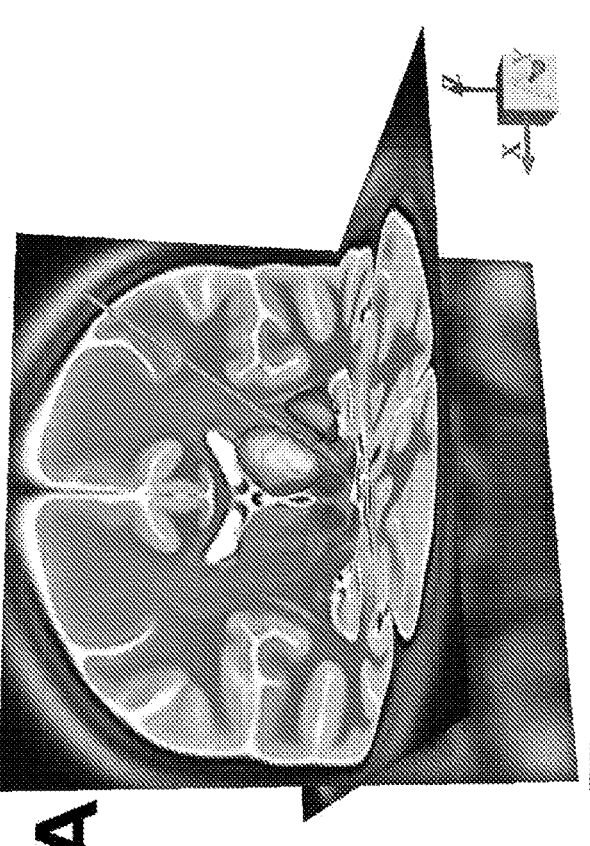
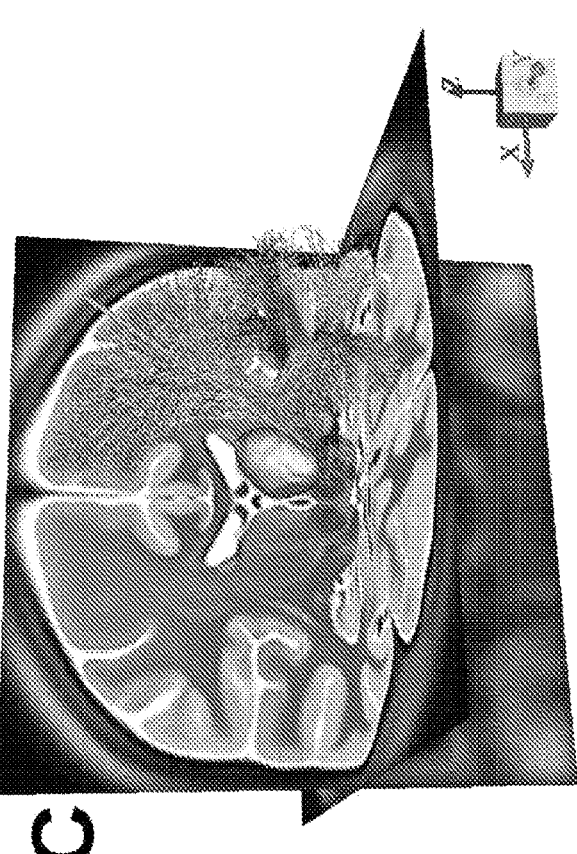
FIG. 10

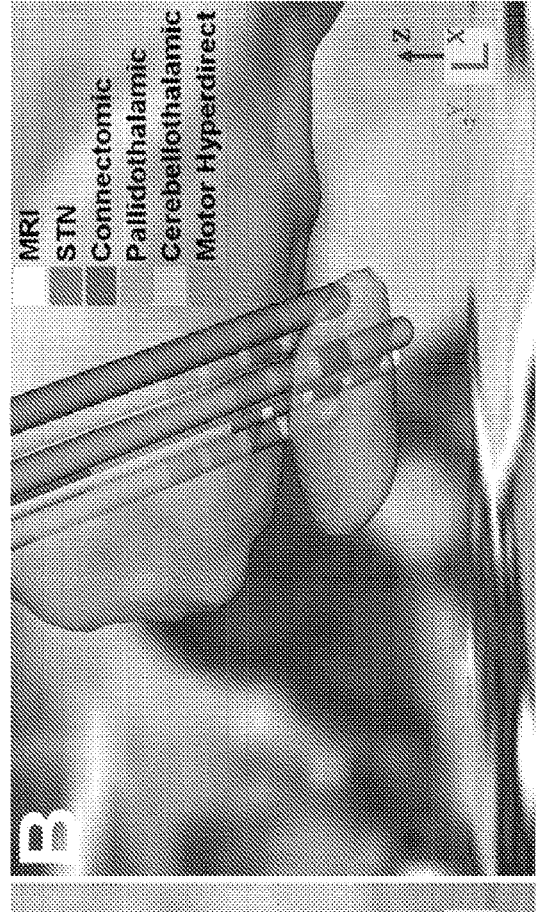
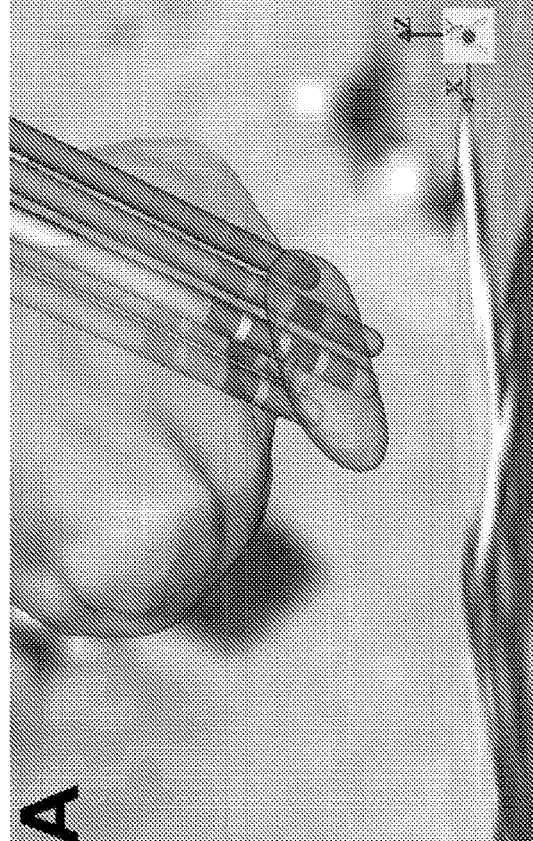
FIG. 13

SYSTEMS, METHODS, AND MEDIA FOR PRESENTING BIOPHYSICAL SIMULATIONS IN AN INTERACTIVE MIXED REALITY ENVIRONMENT

CROSS-REFERENCE TO RELATED APPLICATIONS

This application is the national stage entry of PCT/US2022/032189, filed Jun. 3, 2022, which is based on, claims the benefit of, and claims priority to, U.S. Provisional Patent Application No. 63/202,274, filed Jun. 3, 2021, and U.S. Provisional Patent Application No. 63/263,082, filed Oct. 26, 2021. Each of the preceding applications is hereby incorporated by reference herein in its entirety for all purposes.

STATEMENT REGARDING FEDERALLY SPONSORED RESEARCH

This invention was made with government support under NS105690 awarded by National Institutes of Health. The government has certain rights in the invention.

BACKGROUND

Devices for presenting augmented reality content and/or virtual reality content have recently become more prevalent. It is relatively easy to present virtual reality content to a group of individuals that may or may not share a physical space, as the experience is completely immersive and the content can be presented in a common frame of reference into which one or more users can be inserted. For example, a virtual reality presentation can include a scene captured by one or more cameras (e.g., a nature scene, a sporting event, etc.), and multiple users accessing the content can be placed in the same location within the content, but those users may be presented with different fields of view depending on the orientation selected by the user. As another example, a virtual reality presentation can include computer generated content, and users can participate in an interactive experience in which the various users can be placed within the computer generated content at various locations, and may be able to interact with one another. In such an example, the content can have a universal frame of reference, and the content presented to a user can be based on the user's location and orientation with respect to the universal frame of reference. Although virtual reality content has the potential to allow for interaction between users within the context of the content, interaction between users in their physical space is severely limited due to the completely immersive nature of virtual reality. By contrast, while devices that present augmented reality content can allow users to interact with the physical environment and each other with relative ease, presenting the same content to multiple users is more difficult as different augmented reality devices used by users in the same room may not use the same coordinate system. Accordingly, even if different users were viewing the same augmented reality content, the content may not be presented in correspondence with the same physical space, may have a different orientation, etc. Moreover, augmented reality devices generally are not configured to coordinate to present content according to instructions from a presenter.

Accordingly, new systems, methods, and media for presenting biophysical simulations in an interactive mixed reality environment are desirable.

SUMMARY

In accordance with some embodiments of the disclosed subject matter, systems, methods, and media for presenting biophysical simulations in an interactive mixed reality environment are provided.

In accordance with some embodiments of the disclosed subject matter, a system for presenting biophysical simulations in an interactive mixed reality environment is provided, the system comprising: a head mounted display comprising: a transparent display; a plurality of sensors; and at least one processor, wherein the at least one processor is programmed to: receive medical imaging data associated with a subject; receive, from a server, information useable to visualize a simulation of one or more biophysical processes in connection with a subject-specific anatomical model based on the medical imaging data; cause a visualization of the simulation to be presented, via the transparent display, in connection with the medical imaging data with an instrument presented in a first position; receive, from the server, updated information useable to visualize an updated simulation of the one or more biophysical processes with the instrument in a second position; and cause a visualization of the updated simulation to be presented, via the transparent display, in connection with the medical imaging data with the instrument presented in the second position.

In some embodiments, the medical imaging data comprises T1-weighted magnetic resonance imaging (MRI) data that includes data corresponding to at least a portion of the subject's brain tissue.

In some embodiments, the instrument is a deep brain stimulation (DBS) electrode comprising multiple electrode contacts.

In some embodiments, the visualization includes a representation of the DBS electrode.

In some embodiments, the at least one processor is further programmed to: receive, via an input device, input to manipulate an activation state of one or more of the contacts of the DBS electrode.

In some embodiments, the at least one processor is further programmed to: receive, via an input device, input to manipulate a position of the instrument; and transmit, to the server, instructions based on the input.

In some embodiments, the at least one processor is further programmed to: transmit, to the server, instructions to adjust a position of the instrument to the second position.

In some embodiments, the at least one processor is further programmed to: receive, via an input device, input to manipulate a position of a portion of the subject-specific anatomical model.

In some embodiments, the at least one processor is further programmed to: transmit, to the server, instructions to adjust a position of a portion of the subject-specific anatomical model.

In some embodiments, the at least one processor is further programmed to: receive, via an input device, input to change a portion of the simulation that is visualized.

In some embodiments, the at least one processor is further programmed to: transmit, to the server, instructions to change a portion of the simulation that is visualized.

In accordance with some embodiments of the disclosed subject matter, a system for presenting biophysical simulations in an interactive mixed reality environment is provided, the system comprising: at least one processor, wherein the at least one processor is programmed to: receive a selection of medical imaging data associated with a subject; generate a subject-specific anatomical model based on the medical imaging data; generate a simulation of one or more biophysical processes based on the subject-specific anatomical model and a first position of at least one instrument; generate information useable to visualize the simulation; transmit the information useable to visualize the simulation to a plurality of head-mounted displays (HMDs); receive, from a first HMD of the plurality of HMDs, an instruction to adjust a position of the instrument to a second position; generate an updated simulation of the one or more biophysical processes based on the subject-specific anatomical model and the second position of at least one instrument; generate information useable to visualize the updated simulation; and transmit the information useable to visualize the updated simulation to the plurality of head-mounted displays.

In some embodiments, the medical imaging data comprises T1-weighted magnetic MRI data that includes data corresponding to at least a portion of the subject's brain tissue.

In some embodiments, the medical imaging data comprises T2-weighted magnetic MRI data that includes data corresponding to at least a portion of the subject's brain tissue.

In some embodiments, the visualization includes a representation of the instrument.

In some embodiments, the instrument is a DBS electrode comprising multiple electrode contacts.

In some embodiments, the at least one processor is further programmed to: receive, from the first HMD, instructions to manipulate an activation state of one or more of the contacts of the DBS electrode.

In some embodiments, the instrument comprises a stereoencephalography (SEEG) electrode.

In some embodiments, the instrument comprises a convection enhanced delivery (CED) probe.

In some embodiments, the instrument comprises a laser interstitial thermal therapy (LITT) probe.

In some embodiments, the at least one processor is further programmed to: receive, from the first HMD, instructions to manipulate a position of a portion of the subject-specific anatomical model.

In some embodiments, the at least one processor is further programmed to: receive, from a device associated with the first HMD, instructions to adjust a position of a portion of the subject-specific anatomical model.

In some embodiments, the at least one processor is further programmed to: receive, from an HMD, instructions to change a portion of the updated simulation that is visualized; and generate updated information useable to visualize the updated simulation based on the input to change a portion of the updated simulation that is visualized; and transmit the updated information useable to visualize the updated simulation to the plurality of head-mounted displays.

In some embodiments, the at least one processor is further programmed to: receive, from a device associated with the first HMD, instructions to change a portion of the updated simulation that is visualized.

In some embodiments, the at least one processor is further programmed to: associate a portion of the medical imaging data with an anatomical structure; associate a biophysical model of the anatomical structure with the portion of the subject-specific anatomical model.

In some embodiments, the at least one processor is further programmed to: use a nonlinear transformation matrix and a warp field to associate a portion of a representative anatomical model with the portion of the medical imaging data;

and use the nonlinear transformation matrix and a warp field to adjust a shape of the biophysical model of the anatomical structure.

In some embodiments, the representative anatomical model is a probabilistic brain atlas.

In some embodiments, the biophysical model of the anatomical structure is an axonal pathway.

In some embodiments, the at least one processor is further programmed to: convert the medical imaging data from a first format into a second format.

In some embodiments, the first format is a digital imaging and communications in medicine (DICOM) format.

In some embodiments, the second format is a neruoimaging informatics technology initiative (NIfTI) format.

In accordance with some embodiments of the disclosed subject matter, a method for presenting biophysical simulations in an interactive mixed reality environment is provided, the method comprising: receiving medical imaging data associated with a subject; receiving, from a server, information useable to visualize a simulation of one or more biophysical processes in connection with a subject-specific anatomical model based on the medical imaging data; causing a visualization of the simulation to be presented, via a transparent display, in connection with the medical imaging data with an instrument presented in a first position; receiving, from the server, updated information useable to visualize an updated simulation of the one or more biophysical processes with the instrument in a second position; and causing a visualization of the updated simulation to be presented, via a transparent display, in connection with the medical imaging data with the instrument presented in the second position.

In accordance with some embodiments of the disclosed subject matter, a method for presenting biophysical simulations in an interactive mixed reality environment is provided, the method comprising: receiving a selection of medical imaging data associated with a subject; generating a subject-specific anatomical model based on the medical imaging data; generating a simulation of one or more biophysical processes based on the subject-specific anatomical model and a first position of at least one instrument; generating information useable to visualize the simulation; transmitting the information useable to visualize the simulation to a plurality of head-mounted displays (HMDs); receiving, from a first HMD of the plurality of HMDs, an instruction to adjust a position of the instrument to a second position; generating an updated simulation of the one or more biophysical processes based on the subject-specific anatomical model and the second position of at least one instrument; generating information useable to visualize the updated simulation; and transmitting the information useable to visualize the updated simulation to the plurality of head-mounted displays.

In accordance with some embodiments of the disclosed subject matter, a non-transitory computer readable medium containing computer executable instructions that, when executed by a processor, cause the processor to perform a method for presenting biophysical simulations in an interactive mixed reality environment is provided, the method comprising: receiving medical imaging data associated with a subject; receiving, from a server, information useable to visualize a simulation of one or more biophysical processes in connection with a subject-specific anatomical model based on the medical imaging data; causing a visualization of the simulation to be presented, via a transparent display, in connection with the medical imaging data with an instrument presented in a first position; receiving, from the server, updated information useable to visualize an updated simulation of the one or more biophysical processes with the instrument in a second position; and causing a visualization of the updated simulation to be presented, via a transparent display, in connection with the medical imaging data with the instrument presented in the second position.

In accordance with some embodiments of the disclosed subject matter, a non-transitory computer readable medium containing computer executable instructions that, when executed by a processor, cause the processor to perform a method for presenting biophysical simulations in an interactive mixed reality environment is provided, the method comprising: receiving a selection of medical imaging data associated with a subject; generating a subject-specific anatomical model based on the medical imaging data; generating a simulation of one or more biophysical processes based on the subject-specific anatomical model and a first position of at least one instrument; generating information useable to visualize the simulation; transmitting the information useable to visualize the simulation to a plurality of head-mounted displays (HMDs); receiving, from a first HMD of the plurality of HMDs, an instruction to adjust a position of the instrument to a second position; generating an updated simulation of the one or more biophysical processes based on the subject-specific anatomical model and the second position of at least one instrument; generating information useable to visualize the updated simulation; and transmitting the information useable to visualize the updated simulation to the plurality of head-mounted displays.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 3A shows an example of a system for interacting with a presented biophysical simulation in accordance with some embodiments of the disclosed subject matter.

FIG. 3B shows an example of another system for interacting with a presented biophysical simulation in accordance with some embodiments of the disclosed subject matter.

FIG. 6 shows an example of a process for generating a model useable to generate a biophysical simulation in accordance with some embodiments of the disclosed subject matter.

FIG. 7 shows an example of a process for generating a subject-specific anatomical model in accordance with some embodiments of the disclosed subject matter.

FIG. 10 shows yet another example of biophysical simulations that can be presented in an interactive mixed reality environment in accordance with some embodiments of the disclosed subject matter.

FIG. 13 shows examples of electrode placements based on various DBS surgical plans presented using mechanisms described herein.

DETAILED DESCRIPTION

Figure 1:
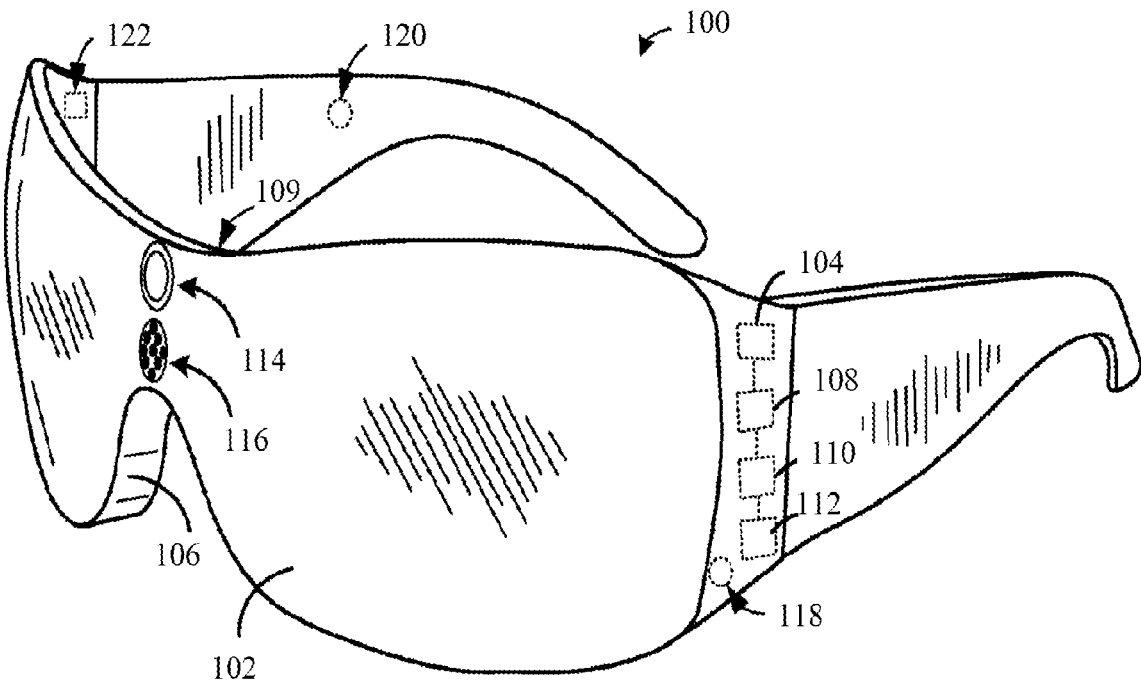
FIG. 1 shows an example of a head mounted display that can be used in accordance with some embodiments of the disclosed subject matter.

Before any embodiments of the disclosed subject matter are explained in detail, it is to be understood that the disclosed subject matter is not limited in its application to the details of construction and the arrangement of components set forth in the following description or illustrated in the following drawings. The disclosed subject matter is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the disclosed subject matter. Various modifications to the illustrated embodiments will be readily apparent to those skilled in the art, and the generic principles herein can be applied to other embodiments and applications without departing from embodiments of the disclosed subject matter. Thus, embodiments of the disclosed subject matter are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the disclosed subject matter. Skilled artisans will recognize the examples provided herein have many useful alternatives and fall within the scope of embodiments of the disclosed subject matter.

In accordance with some embodiments of the disclosed subject matter, mechanisms (which can include systems, methods and/or media) for presenting biophysical simulations in an interactive mixed reality environment are provided.

In some embodiments, mechanisms described herein can be used to implement features that are facilitate more accurate surgical planning, and/or more efficient surgical planning (e.g., by facilitating clearer communication between remote collaborators). For example, in some embodiments, mechanisms described herein can be used to provide holographic visualization and interactive selection of patient-specific brain imaging data and 3D models of patient anatomy. As another example, in some embodiments, mechanisms described herein can be used to combine a patient model with a stereotactic frame system used in the operating room. As yet another example, in some embodiments, mechanisms described herein can be used to facilitate interactive positioning of a DBS electrode(s), and simulation of axonal pathway activation, within a holographic patient model. As still another example, in some embodiments, mechanisms described herein can be used to facilitate group-based interaction with a holographic patient model. In such an example, the group of users can be local (e.g., in the same room) and/or remote (e.g., in different rooms, different cities, different countries, etc.), and every user can be presented with a manipulatable common holographic patient model, thereby facilitating collaborative discussion between users. Audio information from remote users can be transmitted to other HMDs via Voice over Internet Protocol (VOIP). In a particular example, HoloLens 2 headsets can use built-in microphones and speakers that facilitate 3D audio, and users can hear the voices of remote participants in a manner that is consistent with the user's and remote user's relative positions with respect to the hologram.

FIG. 1 shows an example 100 of a head mounted display (HMD) that can be used in accordance with some embodiments of the disclosed subject matter. As shown in FIG. 1, head mounted display 100 can include a display processor 104 and a transparent display 102 that can be used to present images, such as holographic objects, to the eyes of a wearer of HMD 100. In some embodiments, transparent display 102 can be configured to visually augment an appearance of a physical environment to a wearer viewing the physical environment through transparent display 102. For example, in some embodiments, the appearance of the physical environment can be augmented by graphical content (e.g., one or more pixels each having a respective color and brightness) that is presented via transparent display 102 to create a mixed reality (or augmented reality environment). Note that as used herein, mixed reality and augmented reality are meant to convey similar experiences, but a mixed reality environment is intended to convey a more immersive environment than an augmented reality environment. Additionally or alternatively, in some embodiments, transparent display 102 can be configured to render a fully opaque virtual environment (e.g., by using one or more techniques to block the physical environment from being visible through HMD 100). In some embodiments, a non-transparent display can be used in lieu of transparent display 102. In some such embodiments, one or more cameras can be used to generate a real-time representation of at least a portion of the physical environment in which HMD 100 is located. For example, an HMD with a non-transparent display can simulate a mixed reality environment using images of a physical environment and graphics (e.g., 3D models) displayed with the images of the physical environment as though the graphics are physically present within the physical environment. In some such embodiments, HMD 100 can be used to present a virtual reality environment.

As shown in FIG. 1, in some embodiments, transparent display 102 can include one or more image producing elements (e.g., display pixels) located within lenses 106 (such as, for example, pixels of a see-through Organic Light-Emitting Diode (OLED) display). Additionally or alternatively, in some embodiments, transparent display 102 can include a light modulator on an edge of the lenses 106.

In some embodiments, HMD 100 can include various sensors and/or other related systems. For example, HMD 100 can include a gaze tracking system 108 that can include one or more image sensors that can generate gaze tracking data that represents a gaze direction of a wearer's eyes. In some embodiments, gaze tracking system 108 can include any suitable number and arrangement of light sources and/or image sensors. For example, as shown in FIG. 1, the gaze tracking system 108 of HMD 100 can utilize at least one inward facing sensor 109. In some embodiments, a user can be prompted to permit the acquisition and use of gaze information to track a position and/or movement of the user's eyes.

In some embodiments, HMD 100 can include a head tracking system 110 that can utilize one or more motion sensors, such as motion sensors 112 shown in FIG. 1, to capture head pose data that can be used to track a head position of the wearer, for example, by determining the direction and/or orientation of a wearer's head. In some embodiments, head tracking system 110 can include an inertial measurement unit configured as a three-axis or three-degree of freedom position sensor system.

In some embodiments, head tracking system 110 can also support other suitable positioning techniques, such as Global Positioning System (GPS) or other global navigation systems, indoor position tracking systems (e.g., using Bluetooth low energy beacons), etc. Further, while specific examples of position sensor systems have been described, it will be appreciated that any other suitable position sensor systems can be used. For example, head pose and/or movement data can be determined based on sensor information from any suitable combination of sensors mounted on the wearer and/or external to the wearer including but not limited to any number of gyroscopes, accelerometers, inertial measurement units (IMUs), GPS devices, barometers, magnetometers, cameras (e.g., visible light cameras, infrared light cameras, time-of-flight depth cameras, structured light depth cameras, etc.), communication devices (e.g., Wi-Fi antennas/interfaces, Bluetooth, etc.), etc.

In some embodiments, HMD 100 can include an optical sensor system that can utilize one or more outward facing sensors, such as optical sensor 114, to capture image data of the environment. In some embodiments, the captured image data can be used to detect movements captured in the image data, such as gesture-based inputs and/or any other suitable movements by a user wearing HMD 100, by another person in the field of view of optical sensor 114, or by a physical object within the field of view of optical sensor 114. Additionally, in some embodiments, the one or more outward facing sensor(s) can capture 2D image information and/or depth information from the physical environment and/or physical objects within the environment. For example, the outward facing sensor(s) can include a depth camera, a visible light camera, an infrared light camera, a position tracking camera, and/or any other suitable image sensor or combination of image sensors.

In some embodiments, a structured light depth camera can be configured to project a structured illumination (e.g., using infrared light), and to generate image data of illumination reflected from a scene onto which the illumination is projected. In such embodiments, a depth map of the scene can be constructed based on spacing between features in the various regions of an imaged scene. Additionally or alternatively, in some embodiments, a continuous wave time-of-flight depth camera, a pulsed time-of-flight depth camera, and/or other suitable sensor (e.g., LiDAR), etc., can be used to generate depth information. In some embodiments, illumination can be provided by an infrared light source 116, and/or a visible light source.

In some embodiments, the HMD 100 can include a microphone system that can include one or more microphones, such as microphone 118, that can capture audio data. In some embodiments, audio can be presented to the wearer via one or more speakers, such as speaker 120.

In some embodiments, HMD 100 can include a controller, such as controller 122, which can include, for example, a processor and/or memory (as described below in connection with FIG. 4) that are in communication with the various sensors and systems of HMD 100. In some embodiments, controller 122 can store, in memory, instructions that are executable by the processor to receive signal inputs from the sensors, determine a pose of HMD 100, and adjust display properties for content displayed using transparent display 102.

In some embodiments, HMD 100 can have any other suitable features or combination of features, such as features described in U.S. Pat. No. 9,495,801 issued to Microsoft Technology Licensing, LLC, which is hereby incorporated by reference herein in its entirety. The description herein of HMD 100 is merely for illustration of hardware that can be used in connection with the disclosed subject matter. However, the disclosed subject matter can be used with any suitable mixed reality device and/or augmented reality device, such as the HoloLens® and HoloLens 2® made by Microsoft®, and/or devices described in U.S. Pat. Nos. 8,847,988, 8,941,559, U.S. Patent Application Publication No. 2014/0160001, each of which is hereby incorporated by reference herein in its entirety.

Figure 2:
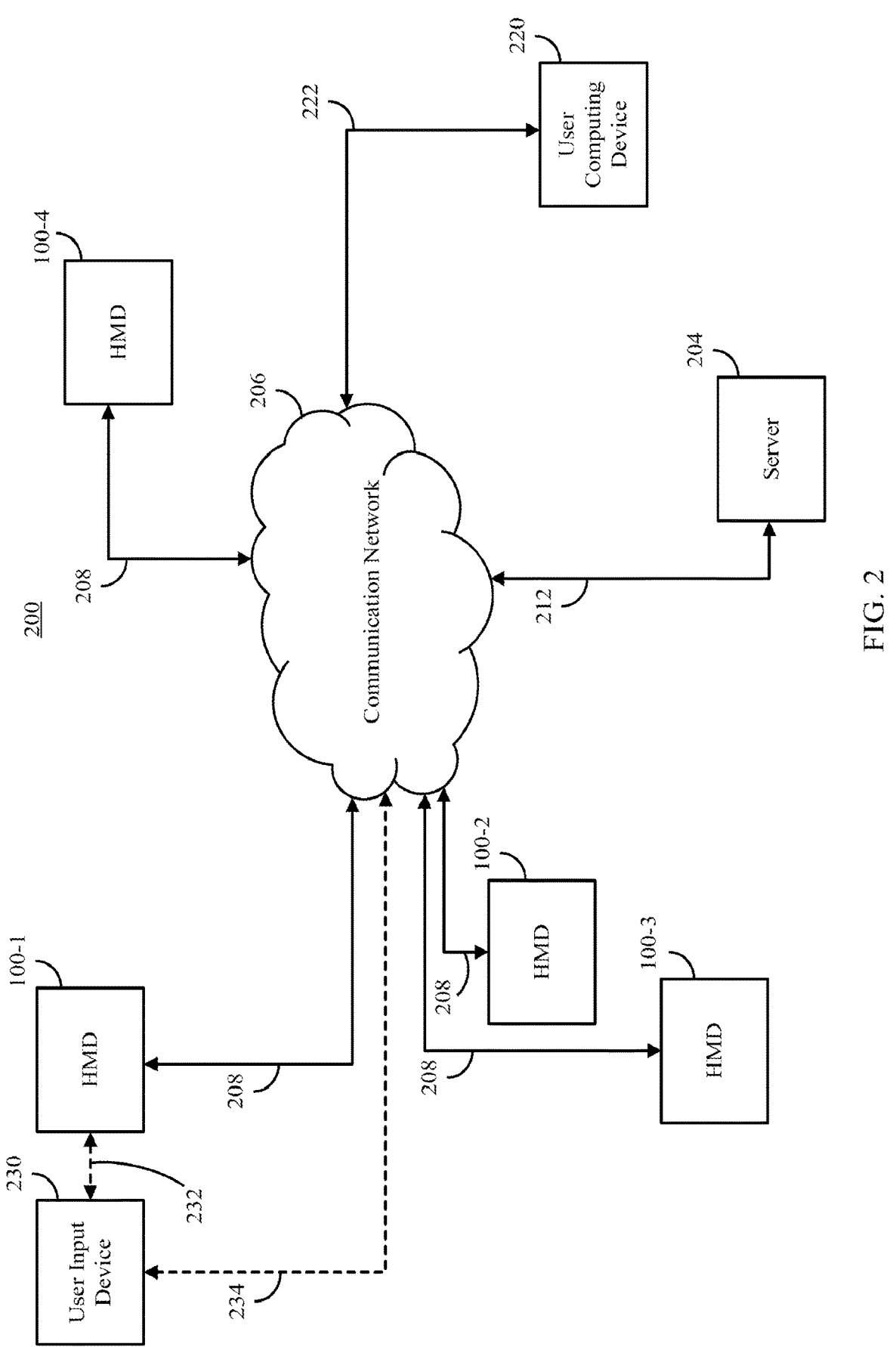
FIG. 2 shows an example of a system of networked head mounted displays in accordance with some embodiments of the disclosed subject matter.

FIG. 2 shows an example 200 of a system of networked HMDs 100 in accordance with some embodiments of the disclosed subject matter. As shown in FIG. 2, system 200 can include various HMDs 100-1 to 100-4, which can be located in the same physical space (e.g., in the same room), and/or in different physical spaces (e.g., not in the same room). For example, HMD 100-1 may be in a first physical space, while HMD 100-2 and 100-3 may be in a second physical space, and HMD 100-4 may be in a third physical space. In such an example, the first, second, and/or third physical spaces may be located relatively close to one another geographically (e.g., within the same building, on the same campus, in the same city, etc.), and/or relatively far from one another (e.g., in different cities, in different states, in different countries, on different continents, etc.). Note that mechanisms described herein can be used with any suitable number of HMDs (e.g., more or less than four shown in FIG. 2).

In some embodiments, system 200 can include a server 204 that can control content that is to be presented by one or more HMDs 100. In some embodiments, server 204 can be implemented using any suitable computing device such as a server computer, an HMD, a tablet computer, a smartphone, a personal computer, a laptop computer, etc. In some embodiments, each HMD 100 can connect to communication network 206 via a communications link 208, and server 204 can connect to communication network 206 via a communications link 212. In some embodiments, a user computing device 220 can connect to communication network 206 via a communications link 222.

Communication network 206 can be any suitable communication network or combination of communication networks. For example, communication network 206 can be a Wi-Fi network (which can include one or more wireless routers, one or more switches, etc.), a peer-to-peer network (e.g., a Bluetooth network, a Zigbee mesh network, etc.), a cellular network (e.g., a 3G network, a 4G network, a 5G network, etc., complying with any suitable standard, such as CDMA, GSM, LTE, LTE Advanced, 5G NR, etc.), a wired network, etc. Communications links 208, 212, and 222 can each be any suitable communications link or combination of communications links, such as a Wi-Fi links, Bluetooth links, cellular links, etc.

In some embodiments, a user can interact with server 204 via user computing device 220 (and/or any other suitable device, such as HMD 100-1) to select content (e.g., a subject-specific anatomical model for a particular subject) that is to be presented by one or more HMDs 100. For example, the user can instruct server 204 to cause HMDs participating in an interactive biophysical simulation to present a visualization of the biophysical simulation (e.g., provided by server 204)

In some embodiments, user computing device 220 can be any suitable computing device or combination of devices, such as a personal computer, a laptop computer, a tablet computer, a smartphone, a wearable computer, a head mounted display (e.g., HMD 100), etc. In some embodiments, a user can select content (e.g., by selecting imaging data associated with a particular subject), select an instrument to be modeled, upload content (e.g., imaging data associated with a particular subject, a model of a particular instrument, a model(s) of an anatomical structure(s), etc.), select a type(s) of biophysical simulation to perform, etc., using user computing device 220 and/or server 204 using any suitable technique or combination of techniques. For example, user computing device 220 can execute an application from memory that is configured to facilitate selection of a subject, uploading content related to the subject, selecting parameters of a simulation, etc. As another example, user computing device 220 can interact with an application executed by another computing device (e.g., server 204, a cloud server, etc.) through network 206 via a web browser executed by computing device 220 and/or another application that facilitates interaction with a remotely executed application.

In some embodiments, each HMD 100 can execute an application(s) that can interact with server 204 (e.g., over communication network 206) to present content associated with a biophysical simulation. When a particular HMD 100 joins a simulation, server 204 can provide content associated with the simulation to the HMD 100. In some embodiments, networking the HMDs 100 with server 204 can facilitate HMDs 100 presenting more content than an HMD 100 would be able to present from memory. Additionally, in some embodiments, networking the HMDs 100 with server 204 can facilitate biophysical simulations (e.g., real-time biophysical simulations) that are computationally intensive and would be impractical to generate using computing resources available locally to HMDs 100. Further, in some embodiments, networking the HMDs 100 with server 204 can facilitate interaction with a simulation by multiple users (e.g., users of HMD 100-1, HMD 100-2, etc.), and can facilitate updated content being presented by the various HMDs 100 participating in the simulation.

In some embodiments, system 200 can determine which content is to be presented by a particular HMD 100 using any suitable technique or combination of techniques. For example, HMD 100 can receive content associated with a simulation from server 204 and/or can present content associated with the simulation from memory. In such an example, HMD 100 can use any suitable technique to determine which content to present.

In some embodiments, HMD 100 can determine that different content is to be presented at any suitable time. Additionally or alternatively, in some embodiments, server 204 can push instructions and/or content to an HMD 100 at any suitable time. For example, server 204 can receive an instruction (e.g., a change in placement of an instrument) to change the content being presented by an HMD(s) 100. In response to such an instruction, server 204 can push an instruction to present the new content (and/or the new content itself) to an appropriate HMD(s) 100.

In some embodiments, one or more HMDs 100 and/or an associated interface device(s) can be used to control what is being presented by HMDs 100 participating in a simulation. For example, in some embodiments, a wearer of HMD 100-1 can interact with a visualization of a biophysical simulation (sometimes referred to herein as a hologram) using any suitable user interface device(s) to control content that is being presented to HMD 100-1 and/or other HMDs 100 participating in a simulation (e.g., HMD 100-2, HMD 100-3, HMD 100-4, etc.). In such an example, the wearer of HMD 100-1 can use any suitable input device or combination of devices, such as an input device of another computing device (e.g., a touchscreen of a computing device such as a smartphone, a tablet computer, a laptop computer, etc.; a mouse and/or keyboard of a computing device such as a laptop computer, a personal computer, etc.), a dedicated input device (e.g., a user input device 230), gestures as inputs to a gesture recognition system (e.g., integrated into HMD 100-1), voice inputs to a voice recognition system, etc.

In some embodiments, sever 204 can communicate additional information to HMDs 100 during presentation of content, such as instructions for one or more of HMDs 100 about how to present the content and/or additional content to be presented. For example, a user of a first HMD 100-1 can use an input device to point (e.g., via a line through space, a dot on the content, the user's hand, etc.) to a particular portion of the content being presented by HMD 100-1 (e.g., a visualization of a biophysical simulation), and server 204 can send instructions to one or more other HMDs 100 presenting the same content that causes each of those HMDs to present supplemental content showing that the user of HMD 100-1 is pointing to a particular portion of the content. In some embodiments, such additional information can be used to control a hologram being presented by HMDs 100. For example, a user of HMD 100-1 can control a presentation via input to HMD 100-1 (and/or any other suitable device), and one or more other HMDs 100 can receive instructions and/or content from server 204 that cause the one or more other HMDs 100 to change which content is being presented and/or how content is being presented in accordance with the input from the user of HMD 100-1.

As another example, a user of a first HMD 100-1 can use an input device (e.g., input device 230, an image sensor of HMD 100-1 capturing an image of a user's hand, input device of another computing device, etc.) to change a position of an instrument (e.g., a deep brain stimulation probe) used to generate a biophysical simulation. In such an example, server 204 can update a position of the instrument based on the input, can generate an updated simulation, and can cause HMDs (e.g., HMD 100-1 and/or other HMDs participating in a simulation) to present a visualization of the updated simulation.

In some embodiments, audio can also be presented with visual content by HMD 100. For example, HMDs 100 can be used to capture audio representing speech, and the audio can be communicated to one or more other HMDs 100 (e.g., via network communication network 206, via server 204, etc.) for presentation to a wearer. In such an example, HMDs 100 can facilitate audio communication between wearers of the HMDs that are participating in a simulation.

As described above, HMDs in system 200 can be located local to each other and/or remote from each other. For example, system 200 can be used to collaborate and/or interact with one or more wearers of HMDs 100 located in one or more remote locations. In some embodiments, two HMDs 100 can be remote from each other if there is not a line of sight between them. For example, two HMDs 100 can be considered remote from each other if they are located in different rooms, regardless of whether they are both connected to the same local area network (LAN) or to different networks. As another example, two HMDs 100 that are connected to different LANs can be considered remote from each other. As yet another example, two HMDs 100 that are connected to different subnets can be considered remote from each other. In some embodiments, two HMDs 100 that are remote from each other can be used to collaborate by representing a remote user with an avatar in connection with a hologram being presented by at least one of the two HMDs 100 (e.g., as described below in connection with FIG. 3B).

In some embodiments, server 204 can be located locally or remotely from HMDs 100. Additionally, in some embodiments, multiple servers 204 can be used (which may be located in different physical locations) to provide different content, perform different functions, provide redundant functions, etc. In some embodiments, one of the HMDs 100 in system 200 can perform one or more of the operations of server 204 described herein, such as instructing other HMDs when to present particular content, for distributing updated information, etc. For example, local HMDs 100 in system 200 can be interconnected to form a mesh network, and an HMD acting as server 204 (e.g., HMD 100-1) can control some operations of another HMD(s) by providing updated information. Additionally, in some embodiments, the HMD acting as server 204 can be a node in the mesh network, and can communicate over another network (e.g., a LAN, cellular, etc.) to receive other information, such as information related to a remote user. In some such embodiments, the HMD acting as server 204 can determine which HMD or HMDs to distribute information to that indicates that an avatar of a remote user is to be presented in connection with a hologram, placement information of the avatar, etc.

Although system 200 is generally described in connection with presenting a mixed reality presentation in a physical environment on a mixed reality device, the system can be configured to present any type of mixed reality (e.g., an augmented reality presentation, an augmented virtuality presentation), or a fully virtual reality presentation. For example, rather than presenting a visualization of a biophysical simulation in a physical environment that a user can physically move through, the content can be presented in a virtual environment that a user can virtually manipulate. Additionally or alternatively, in some embodiments, one or more HMDs in system 200 can be mixed reality devices, while other HMDs can be virtual reality devices. In some embodiments, a user of a virtual reality device can cause a view of a 3D model that is presented to change using any suitable technique, such as inputs received by a user input device (e.g., a game controller, a touchpad, etc.), outputs indicating physical movements of the user (e.g., rotations, translations, etc.), or any other suitable information, Additionally or alternatively, in some embodiments, a user of a virtual reality device can adopt the viewpoint of a mixed reality device that is viewing the same 3D model (e.g., an HMD worn by another user participating in a simulation). In some embodiments, a virtual reality device that is used to participate in a simulation can present one or more portions of video captured by another HMD participating in the simulation (e.g., by a camera that captures 360 degree video of the environment of the other HMD) to generate a mixed reality presentation, can present the 3D model in a virtual environment (e.g., a virtual room) that may or may not be similar to a physical environment of another HMD, or present only the 3D model and information about other users (e.g., present the 3D model in a blank environment (e.g., using a single background color)).

In some embodiments, user input device 230 can communicate with HMD 100-1 via a communications link 232. In some embodiments, communications link 232 can be any suitable communications link that can facilitate communication between user input device 230 and HMD 100-1. For example, communications link 232 can be a wired link (e.g., a USB link, an Ethernet link, a proprietary wired communication link, etc.) and/or a wireless link (e.g., a Bluetooth link, a Wi-Fi link, etc.). In some embodiments, user input device 230 can include any suitable sensor(s) for determining a position of user input device 230 with respect to one or more other devices and/or objects (e.g., HMD 100-1, a particular body part of a wearer of HMD 100-1, a particular structure and/or location in a physical environment of HMD 100-1, etc.), and/or a relative change in position (e.g., based on sensor outputs indicating that user input device 230 has been accelerated in a particular direction, that user input device 230 has been rotated in a certain direction, etc.). For example, in some embodiments, user input device 230 can include one or more accelerometers, one or more gyroscopes, one or more electronic compasses, one or more image sensors, an inertial measurement unit, etc. In some embodiment, in addition to or in lieu of communication link 232, user input device 230 can communicate with HMD 100-1, server 204, and/or any other suitable device(s) via a communication link 234. In some embodiments, communication link 234 can be any suitable communications link or combination of communications links, such as a Wi-Fi link, a Bluetooth link, a cellular link, etc.

In some embodiments, user input device 230 can be used as a pointing device by the wearer of HMD 100-1 to highlight a particular portion of content (e.g., a portion of a hologram being presented by HMD 100-1), to select a particular portion of a hologram (e.g., an instrument, an anatomical structure, etc.), to cause a particular portion of the hologram (e.g., an instrument) to move in a particular way (e.g., in a "click and drag"-type action), etc. For example, a user interface element that highlights a particular region of the simulation can be presented in connection with the visualization of the biophysical simulation in a location that is based on the direction in which user input device 230 is pointed in relation to the hologram. In some embodiments, a second HMD 100-2 that is presenting a second instance of the hologram that includes the same portion of the hologram that is being presented by HMD 100-1 can also present the same user interface element and/or a user interface element at the same location on the hologram (e.g., based on instructions received from server 204, which can be implemented by an HMD such as HMD 100-1, HMD 100-2, and/or another HMD).

In some embodiments, HMD 100-1 and/or server 204 can receive data from user input device 230 indicating movement and/or position data of user input device 230. Based on the data from user input device 230, HMD 100-1 and/or server 204 can determine a location and/or direction of a user interface element to be presented as part of a hologram presented by other HMDs presenting the same content as HMD 100-1.

In some embodiments, user input device 230 can be an integral part of HMD 100-1, which can determine a direction in which HMD 100-1 is pointing with respect to a hologram being presented by HMD 100-1. The information on which direction HMD 100-1 is pointing can be used to infer a direction in which the wearer's eyes are looking (which can, for example, be augmented based on gaze information, in some cases). In some embodiments, the inferred location at which the wearer of HMD 100 is looking can be used as input to position a user interface element with respect to the content (e.g., as a line, a dot, multiple dots, etc., showing where the wearer of HMD 100-1 is looking).

In some embodiments, user input device 230 can be a separate device that can convey location information to HMD 100-1 and/or server 204, which can then be used to generate a user interface element to show where the wearer of HMD 100-1 is pointing. Any suitable technique or combination of techniques can be used to generate the user interface element based on the location information of user input device 230.

FIG. 3A shows an example of a system for interacting with a presented biophysical simulation in accordance with some embodiments of the disclosed subject matter. As shown in FIG. 3A, a user input device 302 can communicate with HMD 100-1 via a communications link 304. In some embodiments, communications link 304 can be any suitable communications link that can facilitate communication between user input device 302 and HMD 100-1. For example, communications link 304 can be a wired link (e.g., a USB link, an Ethernet link, a proprietary wired communication link, etc.) and/or a wireless link (e.g., a Bluetooth link, a Wi-Fi link, etc.). In some embodiments, user input device 302 can include any suitable sensors for determining a position of user input device 302 with respect to one or more other devices and/or objects (e.g., HMD 100-1, station 202, a particular body part of a wearer of HMD 100-1, etc.), and/or a relative change in position (e.g., based on sensor outputs indicating that user input device 302 has been accelerated in a particular direction, that user input device 302 has been rotated in a certain direction, etc.). For example, in some embodiments, user input device 302 can include one or more accelerometers, one or more gyroscopes, one or more electronic compasses, one or more image sensors, an inertial measurement unit, etc.

In some embodiments, user input device 302 can be used as a pointing device by the wearer of HMD 100-1 to highlight a particular portion of content (e.g., a portion of hologram 306-1) being presented by HMD 100-1, to select a particular portion of hologram 306-1 (e.g., an instrument), to cause a particular portion of hologram 306-1 (e.g., an instrument) to move in a particular way (e.g., in a "click and drag"-type action), etc. For example, a user interface element 308 that highlights a particular region of hologram 306-1 can be presented in connection with hologram 306-1 in a location that is based on the direction in which user input device 302 is pointed in relation to hologram 306-1. As shown in FIG. 3A, a second HMD 100-2 that is presenting a second hologram 306-2 that includes the same content that is being presented in hologram 306-1 can also present user interface element 308 (e.g., based on instructions received from server 204, which may be implemented by an HMD such as HMD 100-1, HMD 100-2, and/or another HMD).

In some embodiments, HMD 100-1 and/or server 204 can receive data from user input device 302 indicating movement and/or position data of user input device 302. Based on the data from user input device 302, HMD 100-1 and/or server 204 can determine a location and/or direction of user interface element 308 to be presented as part of hologram 306-1 (and as part of any other hologram being presented by another HMD 100 presenting the same content as hologram 306-2). Additionally or alternatively, in some embodiments, based on the data from user input device 302, HMD 100-1 and/or server 204 can determine a new location and/or direction of an instrument that is part of a biophysical simulation being visualized via hologram 306-1, and the new location and/or direction of the instrument can be used to generate an updated biophysical simulation which can be visualized by each HMD participating in the simulation (e.g., via hologram 306-1 and hologram 306-2).

As described above, in some embodiments, user input device 302 can be an integral part of HMD 100-1, which can determine a direction in which HMD 100-1 is pointing with respect to hologram 306-1.

In some embodiments, user input device 302 can be a separate device that can convey location information to HMD 100-1 and/or server 204, which can then be used to generate user interface element 308 to show where the wearer of HMD 100-1 is pointing. Any suitable technique or combination of techniques can be used to generate the user interface element based on the location information of user input device 302. For example, in some embodiments, HMD 100-1 and/or server 204 can determine a location of user input device 302 with respect to a part of the wearer's body (e.g., the center of the user's body, which can, for example, be inferred based on the location of HMD 100-1) and can draw a line that intersects that part of the wearer's body and user input device 302. As another example, in some embodiments, HMD 100-1 and/or server 204 can determine a location and/or orientation of user input device 302 with respect to hologram 306-1, and can draw a line from user input device 302 based on the location and orientation. In such an example, the location of user input device 302 may need to be calibrated more precisely than in the previous example, and may be calculated in the local coordinates of the hologram. Accordingly, in such an example, the accuracy of the location at which user interface element 308 is presented can vary based on the accuracy of the calibration, the distance from an anchor point (or other location reference) of hologram 306-1 (as distances farther from the anchor point may be determined less accurately), etc.

As yet another example, in some embodiments, HMD 100-1 and/or server 204 can receive a first input from user input device 302, which can signal that a wearer of HMD 100-1 is initiating the generation of user interface element 308 on hologram 306-1. Upon receiving the first user input (e.g., a first button press), HMD 100-1 and/or server 204 can generate user interface element 308 at a default location based on the wearer's current location relative to hologram 306-1 (e.g., a line straight out from the user's body toward the center of hologram 306-1). After the first button press, HMD 100 and/or server 204 can change the direction of the user interface element (e.g., the point at which the line crosses hologram 306-1 and/or the direction in which the line intersects hologram 306-1) based on information received from user input device 302. In such an example, after a first button press, the wearer can translate user interface device 302 to raise/lower and/or move left/right the point at which the line intersects hologram 306-1 (which can, e.g., cause movement of user interface element 308, as shown by dotted lines in FIG. 3A), and can rotate user input device 302 to change an orientation at which the line intersects hologram 306-1. In some embodiments, upon receiving a second user input, HMD 100-1 and/or server 204 can freeze the position and/or orientation of user interface element 308 with respect to hologram 306-1. Such a control scheme for the line to be presented in hologram 306-1 can have some similarity to the operation of a mouse for controlling a pointer (e.g., a cursor) in a 2D graphical user interface. Alternatively, in some embodiments, upon receiving a second user input, HMD 100-1 and/or server 204 can select a user interface element (e.g., an instrument being used in the biophysical simulation, not shown in FIG. 3A), and further movements of user input device 302 can be used as instructions to adjust a position and/or orientation of the user interface element.

FIG. 3B shows an example of another system for interacting with a presented biophysical simulation in accordance with some embodiments of the disclosed subject matter. As shown in FIG. 3B, a first HMD 100-1 worn by a first user 312 at a first location can present a hologram 306-1. In some embodiments, HMD 100-1 can track the position of a hand 314 of user 312 with respect to hologram 306-1. In some embodiments, HMD 100-1 can use any suitable technique or combination of techniques to track the location and/or orientation of the user's hand. For example, HMD 100-1 can track the location of the user's hand visually using images produced by one or more image sensors (e.g., optical sensor 114) and/or any other suitable data, such as depth information in a scene. As another example, HMD 100-1 can track the location of the user's hand using one or more sensors to sense a position of a device held by (or otherwise attached) to the user's hand.

In some embodiments, HMD 100-1 can transmit information to server 204 indicating the position of HMD 100-1 and the user's hand with respect to hologram 306-1. As shown in FIG. 3B, server 204 can transmit information to a second HMD 100-2 presenting a hologram 306-2 that includes the same content as hologram 306-1, where the information can indicate a position at which to present an avatar 316 representing user 312 of HMD 100-1 with respect to hologram 306-2. HMD 100-2 can use such information to present avatar 316 and a hand element 318 with hologram 306-2 to a second user 320. In some embodiments, HMD 100-1 can be caused to present an avatar of user 320 in connection with hologram 306-1 (not shown). Note that this is merely an example, and an avatar, such as avatar 316, can be presented regardless of whether a position of a hand of the user is tracked.

Figure 4:
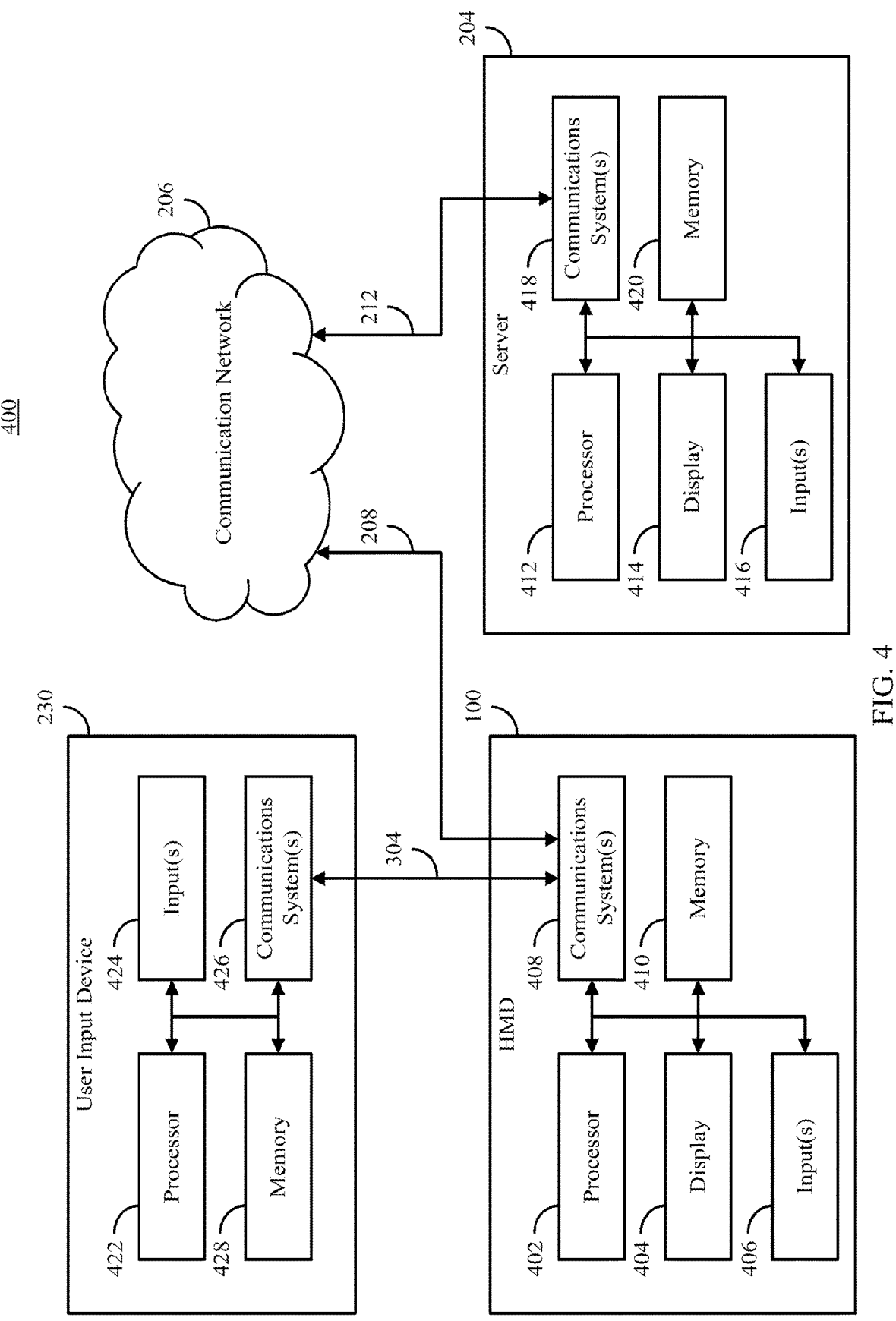
FIG. 4 shows an example of hardware that can be used to implement at least one head mounted display, at least one server, and at least one user input device in accordance with some embodiments of the disclosed subject matter.

FIG. 4 shows an example 400 of hardware that can be used to implement at least one of HMD 100, server 204 and user input device 230 in accordance with some embodiments of the disclosed subject matter. As shown in FIG. 4, in some embodiments, HMD 100 can include a processor 402, a display 404, one or more inputs 406, one or more communication systems 408, and/or memory 410. In some embodiments, processor 402 can be any suitable hardware processor or combination of processors, such as a central processing unit (CPU), a graphics processing unit (GPU), etc. In some embodiments, display 404 can include any suitable display device(s), such as a transparent display as described above in connection with FIG. 1. In some embodiments, inputs 406 can include any suitable input device(s) and/or sensor(s) that can be used to receive user input, such as gaze tracking system 108, head tracking system 110, motion sensors 112, optical sensor 114, microphone 118, etc.

In some embodiments, communications systems 408 can include any suitable hardware, firmware, and/or software for communicating information over communication network 206 and/or any other suitable communication networks. For example, communications systems 408 can include one or more transceivers, one or more communication chips and/or chip sets, etc. In a more particular example, communications systems 408 can include hardware, firmware and/or software that can be used to establish a Wi-Fi connection, a Bluetooth connection, a cellular connection, etc.

In some embodiments, memory 410 can include any suitable storage device or devices that can be used to store instructions, values, etc., that can be used, for example, by processor 402 to present content using display 404, to communicate with server 204 via communications system(s) 408, etc. Memory 410 can include any suitable volatile memory, non-volatile memory, storage, any other suitable type of storage medium, or any suitable combination thereof. For example, memory 410 can include random access memory (RAM), read-only memory (ROM), electronically erasable programmable read-only memory (EEPROM), one or more flash drives, one or more hard disks, one or more solid state drives, one or more optical drives, etc. In some embodiments, memory 410 can have encoded thereon a computer program for controlling operation of HMD 100. In some such embodiments, processor 402 can execute at least a portion of the computer program to present content (e.g., one or more holograms), receive content from server 204, transmit information to server 204, etc. In some embodiments, HMD 100 can use any suitable hardware and/or software for rendering the content received from server 204, such as Unity 3D available from Unity Technologies. Additionally, in some embodiments, any suitable communications protocols can be used to communicate control data, image data, audio, etc., between HMDs 100 and server 204, such as networking software available from Unity Technologies.

In some embodiments, server 204 can include a processor 412, a display 414, one or more inputs 416, one or more communication systems 418, and/or memory 420. In some embodiments, processor 412 can be any suitable hardware processor or combination of processors, such as a central processing unit, a graphics processing unit, etc. In some embodiments, display 414 can include any suitable display devices, such as a computer monitor, a touchscreen, a television, etc. In some embodiments, inputs 416 can include any suitable input devices and/or sensors that can be used to receive user input, such as a keyboard, a mouse, a touchscreen, a microphone, etc.

In some embodiments, communications systems 418 can include any suitable hardware, firmware, and/or software for communicating information over communication network 206 and/or any other suitable communication networks. For example, communications systems 418 can include one or more transceivers, one or more communication chips and/or chip sets, etc. In a more particular example, communications systems 418 can include hardware, firmware and/or software that can be used to establish a Wi-Fi connection, a Bluetooth connection, a cellular connection, etc.

In some embodiments, memory 420 can include any suitable storage device or devices that can be used to store instructions, values, etc., that can be used, for example, by processor 412 to present content using display 414, to communication with one or more HMDs 100, etc. Memory 420 can include any suitable volatile memory, non-volatile memory, storage, any other suitable type of storage medium, or any suitable combination thereof. For example, memory 420 can include RAM, ROM, EEPROM, one or more flash drives, one or more hard disks, one or more solid state drives, one or more optical drives, etc. In some embodiments, memory 420 can have encoded thereon a server program for controlling operation of server 204. In such embodiments, processor 412 can execute at least a portion of the computer program to transmit content (e.g., one or more holograms) to one or more HMDs 100, receive content from one or more HMDs 100, receive instructions from one or more devices (e.g., HMD 100-1, user input device 230, another server, a personal computer, a laptop computer, a tablet computer, a smartphone, etc.).

In some embodiments, user input device 230 can include a processor 422, one or more inputs 224, one or more communication systems 426, and/or memory 428. In some embodiments, processor 422 can be any suitable hardware processor or combination of processors, such as a central processing unit, a graphics processing unit, etc. In some embodiments, inputs 424 can include any suitable input devices and/or sensors that can be used to receive user input, such as one or more physical or software buttons, one or movement sensors, a microphone, a touchpad, etc.

In some embodiments, communications systems 426 can include any suitable hardware, firmware, and/or software for communicating information over communications link 232, communications link 234, and/or any other suitable communications links. For example, communications systems 426 can include one or more transceivers, one or more communication chips and/or chip sets, etc. In a more particular example, communications systems 426 can include hardware, firmware and/or software that can be used to establish a Wi-Fi connection, a Bluetooth connection, a cellular connection, etc.

In some embodiments, memory 428 can include any suitable storage device or devices that can be used to store instructions, values, etc., that can be used, for example, by processor 422 to determine when input (e.g., user input) is received, to record sensor data, to communicate sensor data with one or more HMDs 100, etc. Memory 428 can include any suitable volatile memory, non-volatile memory, storage, any other suitable type of storage medium, or any suitable combination thereof. For example, memory 428 can include RAM, ROM, EEPROM, one or more flash drives, one or more hard disks, one or more solid state drives, one or more optical drives, etc. In some embodiments, memory 428 can have encoded thereon a computer program for controlling operation of user input device 230. In such embodiments, processor 422 can execute at least a portion of the computer program to transmit data (e.g., representing sensor outputs) to one or more HMDs 100, to transmit data (e.g., representing sensor outputs) to one or more servers 204, etc.

Figure 5:
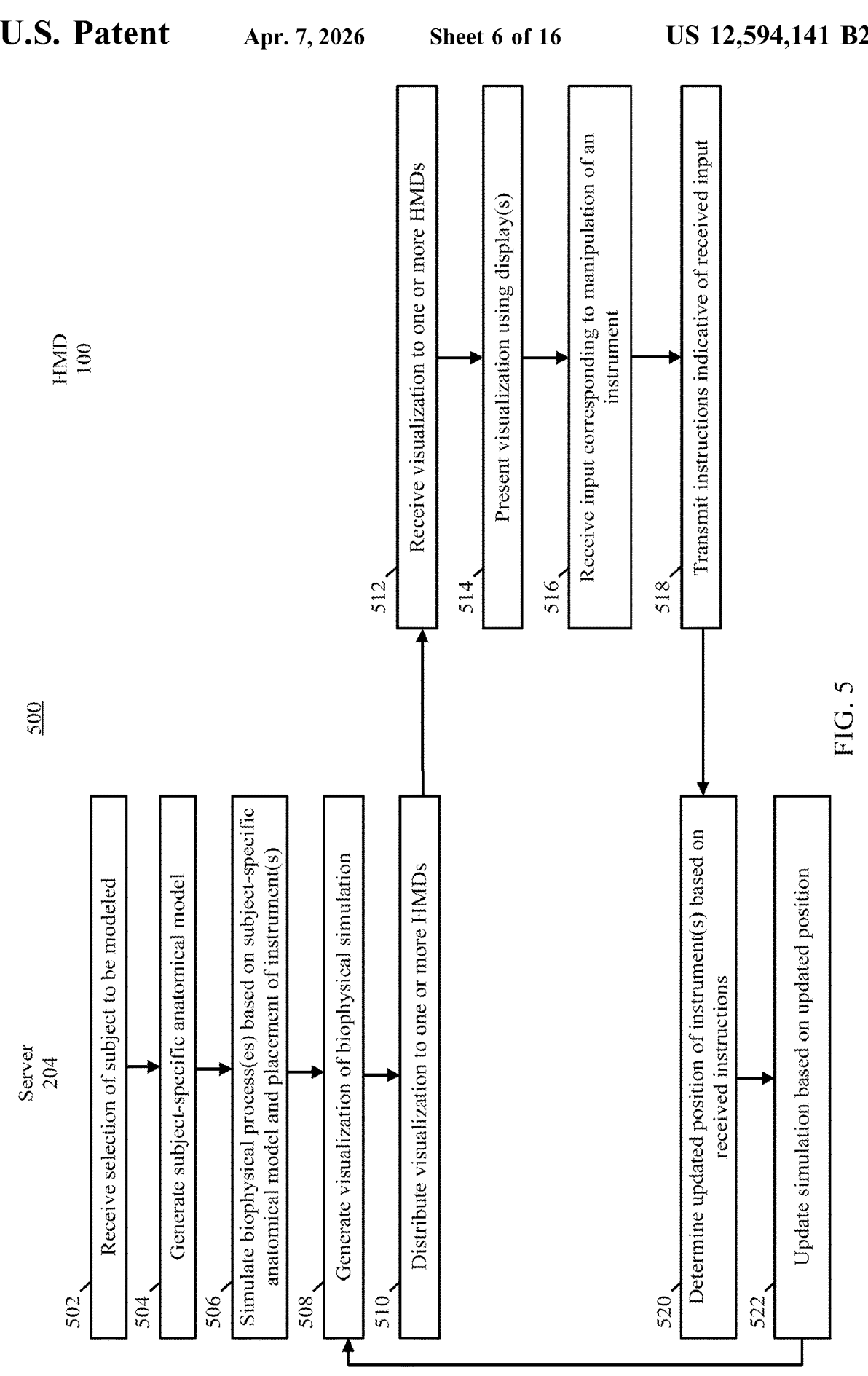
FIG. 5 shows an example of a process among a server generating a biophysical simulation and a head mounted display receiving and presenting content representing the biophysical simulation in accordance with some embodiments of the disclosed subject matter.

FIG. 5 shows an example 500 of a process among a server generating a biophysical simulation and a head mounted display receiving and presenting content representing the biophysical simulation in accordance with some embodiments of the disclosed subject matter. At 502, server 204 can receive a selection of a subject to be modeled from any suitable source. For example, server 204 can receive a selection from an HMD 100. As another example, server 204 can receive a selection from a computing device (e.g., user computing device 220, another server). In some embodiments, server 204 can receive the selection over a local communication network and/or a non-local communication network (e.g., a device from which a selection is received can be local to server 204 or remote from server 204).

Additionally, at 502, server 204 can receive a selection of a subject to be modeled from using any suitable technique or combination of techniques. For example, server 204 can receive identifying information of a subject, such as a medical record number associated with the subject, a name of the subject, a registry number (sometimes referred to as an accession number) associated with the subject, a portion of a social security number associated with the subject, a name of the subject, any other identifier (e.g., a patient ID) associated with the subject, and/or any other suitable identifying information. As another example, server 204 can receive identifying information of medical image data to be used to generate a model, such as a filename, a location, a study identification number, etc.

At 504, server 204 can generate a subject-specific anatomical model using medical image data associated with the subject. For example, server 204 can generate the subject-specific anatomical model using computed tomography (CT) data associated with the subject. As another example, server 204 can generate the subject-specific anatomical model using magnetic resonance imaging (MRI) data associated with the subject.

As described below in connection with FIG. 6, in some embodiments, server 204 can receive the medical imaging data from any suitable source and/or at any suitable time.

In some embodiments, server 204 can generate the subject-specific anatomical model from the medical image data using any suitable technique or combination of techniques. For example, server 204 can use a representative anatomical model (e.g., an anatomical atlas) to identify particular portions of the medical imaging data as corresponding to particular anatomical structures. As another example, server 204 can use machine learning techniques to identify particular portions of the medical imaging data as corresponding to particular anatomical structures. As yet another example, server 204 can receive manual or semi-manual (e.g., machine assisted) input identifying particular portions of the medical imaging data as corresponding to particular anatomical structures.

As a more particular example, server 204 can load brain imaging data, 3D anatomical volumes, and axonal pathway models associated with a subject. In such an example, the foundation for the model can be the patient-specific MRI data, where the highest quality pre-operative T1-weighted image can generally be used as the reference image for co-registration of all other datasets. When available, the CT or MRI with the stereotactic coordinate system fiducials can be loaded into the model to facilitate direct integration of the surgical frame system into the planning environment. However, mechanisms described herein can also function in the anterior/posterior commissural (AC-PC) coordinate system, with the mid-commissural point (MCP) defined as the origin. The chosen coordinate system can provide the basis for positioning of a DBS electrode(s) in the patient brain model.

As another more particular example, mechanisms described herein can use patient-specific imaging data in parallel with the CIT168 brain atlas volumes and axonal pathways (e.g., described in Petersen et al., "Holographic reconstruction of axonal pathways in the human brain," Neuron, 2019; 104:1056-1064). In such an example, server 204 can fit 3D anatomical models of the brain nuclei and axonal pathways to patient-specific imaging data (e.g., MRI data) via non-linear warping (e.g., as described below in connection with 704 of FIG. 7). A user can then position the DBS lead based on the patient-specific imaging data (e.g., as described below in connection with 516 of FIG. 5), and can evaluate the simulated axonal connectivity associated with stimulation through the electrode contacts (e.g., as described below in connection with FIG. 12).

In some embodiments, server 204 can use one or more additional biophysical models (e.g., of a particular structure(s)) that can be associated with the anatomical model, and used to generate at least a portion of a biophysical simulation.

In some embodiments, the subject-specific anatomical model can include a 3D representation of bone, blood vessels, muscle, nerve tissue, organ tissue, and/or any other suitable anatomical structure. For example, a subject-specific anatomical model generated for planning a cranial neurosurgical trajectory can include a 3D representation of the skull, intracranial blood vessels, cortex, nuclei (e.g., a cluster of neurons in the central nervous system), axonal pathways, neurons, and/or any other suitable anatomical structure(s).

In some embodiments, a biophysical model can include a geometric shape (e.g., a sphere), one or more analytical equations, results from complex finite element models of electric fields, results from complex finite element models of heat transfer, results from complex finite element models of fluid dynamics, etc.

At 506, server 204 can simulate one or more biophysical processes based on the subject-specific anatomical model generated at 504, and a placement of one or more instruments. In some embodiments, server 204 can simulate any suitable biophysical process or processes using any suitable technique or combination of techniques. For example, server 204 can simulate stimulation (e.g., electrical stimulation) provided via an instrument. As another example, server 204 can simulate thermal processes (e.g., heating that can cause tissue ablation, etc.). As still another example, server 204 can simulate diffusion processes (e.g., of one or more chemical agents).

At 508, server 204 can generate one or more visualizations of the biophysical simulation and/or information that can be used to render one or more visualizations using any suitable technique or combination of techniques. For example, server 204 can generate a three dimensional (3D) model based on the medical imaging data used to generate the subject-specific anatomical model that shows results of one or more biophysical simulations. For example, as described below in connection with FIGS. 8 and 9, server 204 can assign a color to one or more voxels of the 3D model to represent particular anatomical structures. As another example, server 204 can generate lines, volumes, and/or any other suitable features that represent one or more biophysical processes that have been simulated.

In a particular example, server 204 can generate 3D curves representing subject-specific axonal pathways, in which particular colors are assigned to different pathways. In another more particular example, server 204 can generate 3D volumes representing subject-specific nuclei, in which particular colors are assigned to different structures. As yet another more particular example, server 204 can generate a visualization in which particular pathways are presented in colors based on a biophysical process being simulated (e.g., showing a magnitude of extracellular voltage). As still another more particular example, server 204 can generate a visualization in which activated pathways are presented in a particular color. In some embodiments, server 204 can include a model of one or more instruments used in the visualization in the visualization at a particular position and orientation with respect to the subject-specific anatomical model, such that a user can view the position of the instrument(s) in connection with one or more biophysical process(es).

In some embodiments, server 204 can format the visualization in any suitable format. For example, server 204 can format the visualization as an FBX file (e.g., having file extension .fbx), as an OBJ file (e.g., having file extension .obj), as a glTF or GLB file (e.g., having a gift or .glb extension), etc.

At 510, server 204 can distribute a visualization of the simulation and/or information that can be used to generate a visualization of the simulation to one or more HMDs that are participating in the simulation using any suitable technique or combination of techniques. In some embodiments, server 204 can transmit a file that includes information that can be used to generate a visualization of the simulation.

As described above in connection with FIG. 2, server 204 can distribute the visualization to HMDs over a communication network, such as a LAN and/or WAN (e.g., the Internet).

At 512, an HMD participating in the simulation (e.g., any HMD 100, such as HMD 100-1), can receive the visualization of the simulation and/or information that can be used to generate a visualization of the simulation using any suitable technique or combination of techniques.

At 514, HMD 100 can present the visualization using a display or displays (e.g., transparent display 102). In some embodiments, HMD 100 can render the visualization as a 3D volume based on a file and/or instructions received from server 204 at 512. Additionally or alternatively, in some embodiments, HMD 100 can render the visualization based on data stored by HMD 100 (e.g., in memory) and instructions received from server 204 at 512.

In some embodiments, at 514, HMD 100 and other HMDs (e.g., each HMD participating in a particular session, which can include remote HMDs and/or local HMDs) can be used to present the same hologram (e.g., potentially from different points of view, based on the HMD's current location and orientation), which can include the exact same content. In some embodiments, a sensor(s) (e.g., a depth camera, such as a Kinect sensor implemented in a Hololens 2 sold by Microsoft, Corp.) can be used by HMD 100 to substantially continuously (e.g., in real time) determine a location of HMD 100 and/or a user of HMD 100 (e.g., a wearer of HMD 100) with respect to a physical environment of HMD 100 (e.g., a room in which HMD 100 is located). As a user moves, the sensor(s) can monitor the position of HMD 100 with respect to the environment, which can facilitate the HMD to anchor the holographic simulation in a particular location for that user (e.g., allowing the user to move around the holographic simulation).

Figure 11:
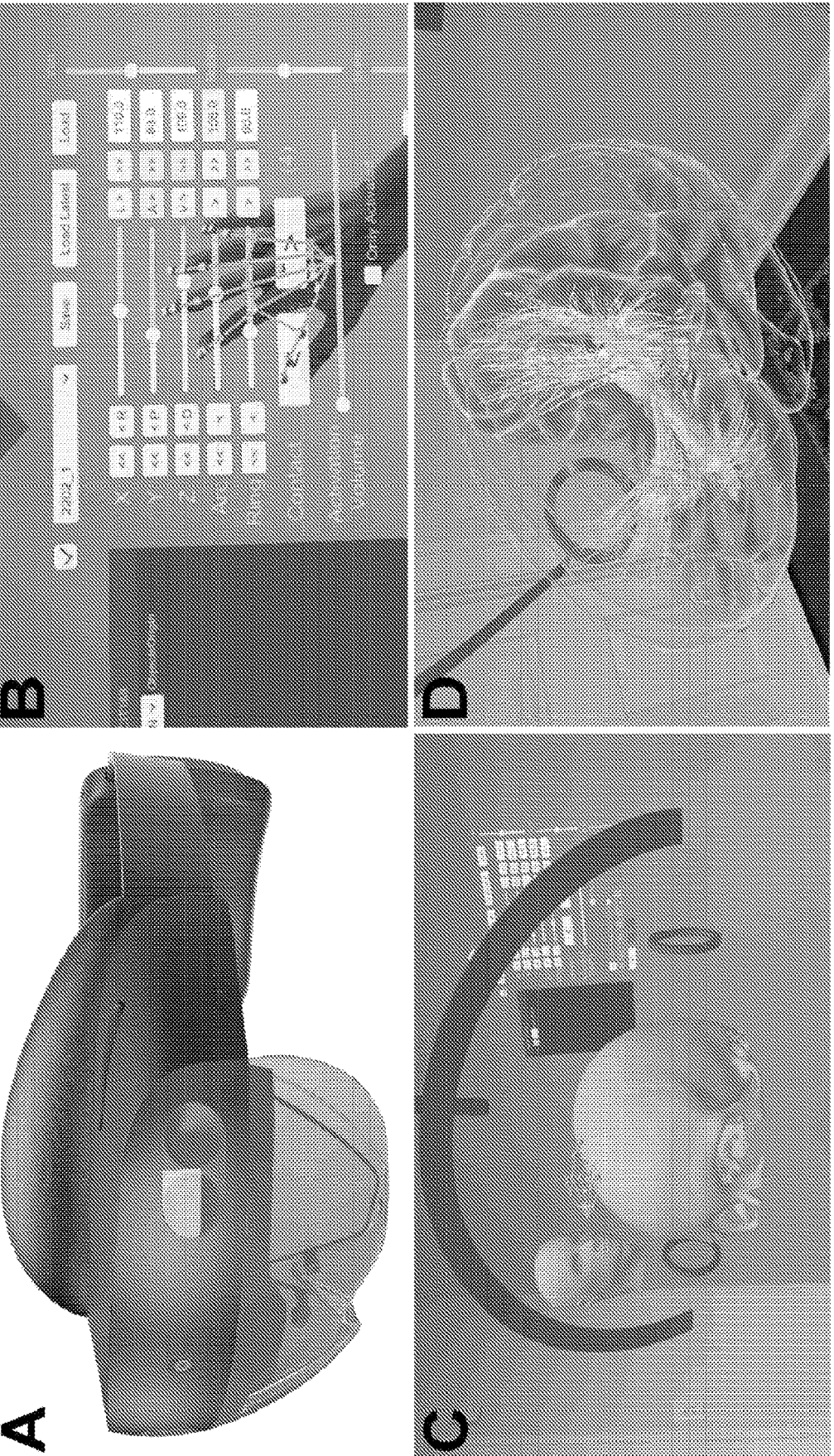
FIG. 11 shows an example of a head mounted display that can be used in accordance with some embodiments of the disclosed subject matter, and examples of user interfaces that can be presented in an interactive mixed reality environment in accordance with some embodiments of the disclosed subject matter.

In some embodiments, when multiple HMDs are local, users can see each other through the transparent display of the HMD, and can ascertain other users' location with respect to the holographic simulation based on the relationship between the holographic simulation presented by the HMD worn by the user and the position of the other user(s) in the environment. Additionally or alternatively, in some embodiments, when a user is remote, HMD 100 can receive location information associated with a remote HMD, and can present an avatar (e.g., a head) at a position with respect to the holographic simulation that identifies the remote user's position in the holographic scene (e.g., as shown in FIG. 11, panel c). In some embodiments, a sensor(s) (e.g., a depth camera, such as a Kinect sensor implemented in a Hololens 2 sold by Microsoft, Corp.; a handheld user input device; etc.) can be used by HMD 100 to recognize and/or track a position of the hands of the user. This can facilitate presentation of a model of the hand (e.g., a wire frame model) to track the movement of individual fingers of a user. Additionally, in some embodiments, when a user is remote, HMD 100 can receive location information associated with a hand (e.g., tracked by the remote HMD), and can present an avatar (e.g., of a hand) at a position with respect to the holographic simulation that identifies the hand position and pose of a remote user's hand in the holographic scene (e.g., as shown in FIG. 11, panel c).

At 516, HMD 100 can receive input corresponding to manipulation of an instrument(s) and/or components of the subject-specific anatomical model used to generate the simulation. For example, a wearer of HMD 100 can manipulate a position of an instrument (e.g., a DBS probe, stereo-encephalography (SEEG) electrode(s), a convection enhanced delivery (CED) probe, a laser interstitial thermal therapy (LITT) probe, etc.) with respect to the visualization using any suitable input device (e.g., an input device of another computing device, such as user computing device 220, a separate input device, such as user input device 230, and/or one or more sensors of HMD 100). As another example, a wearer of HMD 100 can manipulate a position of an anatomical structure (e.g., a nucleus). In a more particular example, a wearer of HMD 100 can manually adjust a position of an anatomical structure to better correspond to the subject's anatomy. In some embodiments, HMD 100 can receive user input corresponding to manipulation of an instrument and/or components of the subject-specific anatomical model, and/or manipulation of a user interface element(s), using any suitable technique or combination of techniques. For example, HMD 100 can receive input via a separate input device that is in communication with HMD 100, such as user input device 230. As another example, HMD 100 can detect a position of an index fingertip of a wearer of HMD 100 (e.g., using one or more sensors), and can use the position of the index finger with respect to the holographic simulation and/or a graphical user interface presented in connection with the holographic simulation to receive user input.

Figure 8:
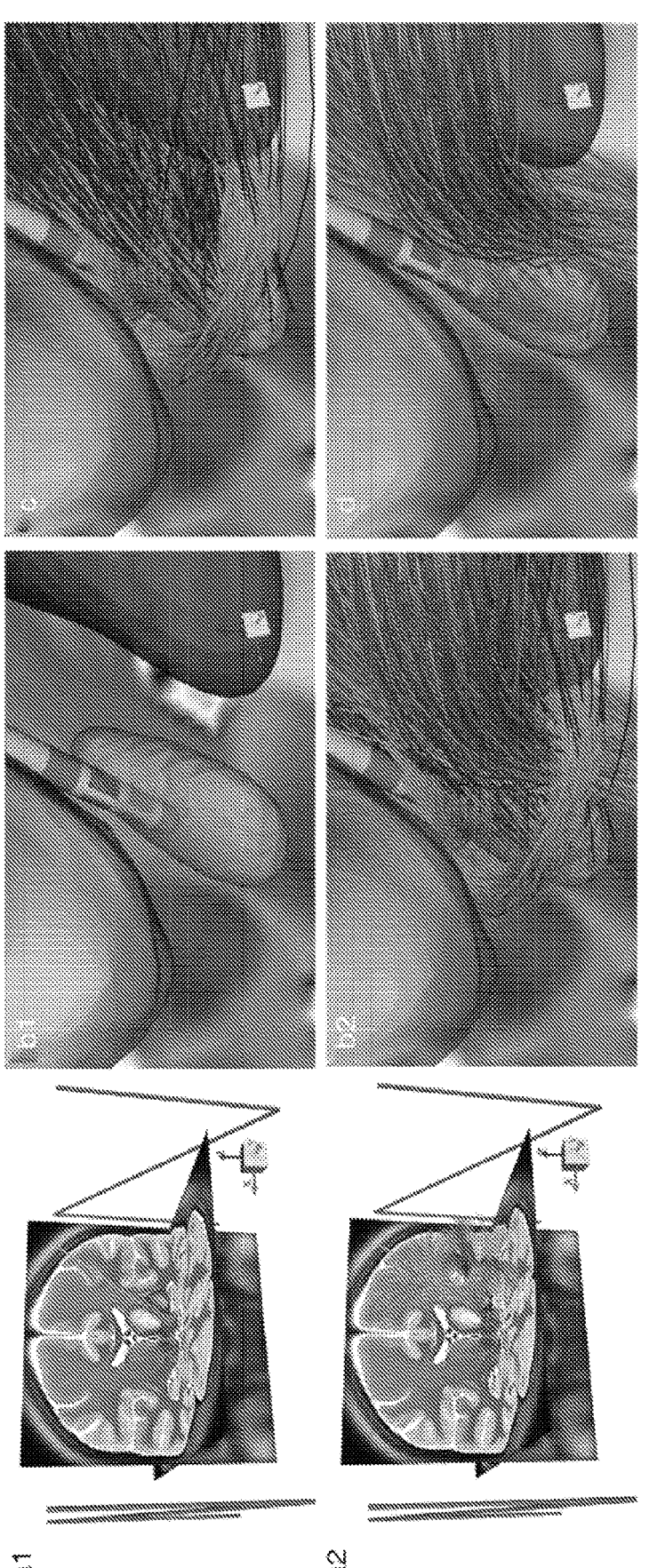
FIG. 8 shows an example of biophysical simulations that can be presented in an interactive mixed reality environment in accordance with some embodiments of the disclosed subject matter.

Additionally or alternatively, at 516, HMD 100 can receive input indicating manipulation of the simulation. For example, HMD can receive input to change which portions of the simulation are presented, which biophysical simulation results are presented, etc. For example, as shown in FIG. 8, HMD 100 can receive input to cause axonal pathways to be presented or omitted from presentation. In a more particular example, HMD 100 can receive input to cause specific pathways (e.g., associated with the basal ganglia, associated with the internal capsule, etc.) to be presented, while presentation of other pathways is inhibited. As another more particular example, HMD 100 can receive input to cause results of a stimulation simulation to be presented (or inhibited). As yet another more particular example, HMD 100 can receive input to cause results of a simulation of heat generation and/or dissipation to be to be presented (or inhibited). As still another example, HMD 100 can receive input to cause a change in a state of an instrument(s) associated with the simulation. In a more particular example, HMD 100 can receive input to cause a change in which contact(s) of a DBS electrode is active and/or inactive. In another more particular example, HMD 100 can receive input to cause a change in an operational state of an SEEG electrode(s), an operational state of a CED probe, an operational state of a LITT probe, etc.

In some embodiments, HMD 100 can be configured to present a control panel in connection with a holographic simulation, which can be used to receive input to adjust the simulation (e.g., as shown in FIG. 11, panel (c). For example, in some embodiments, a position of a user's hand and/or a particular finger (e.g., determined based on sensor data, as described above) can be used to determine whether a user has manipulated a user interface element presented as part of the control panel (e.g., to determine whether a buttons has been pressed, or a slider has been moved on the control panel to turn on/off different data elements, to position the DBS electrode, to adjust the activation volume, to select the desired MRI slices for visualization, etc.). In some embodiments, the control panel can be moved to any location within the holographic scene by grabbing it with an avatar hand and dragging it to the desired location. Additionally or alternatively, in some embodiments, the control panel can be presented using a separate computing device (e.g., computing device 230, such as a tablet computer) that is linked to one or more HMDs, as some users prefer this mode of interaction with the simulation. In some embodiments, user's (e.g., local users and remote users) can share a single control panel (e.g., the control panel can be presented at a common location with respect to the holographic simulation), which can allow users to observe when another user manipulates the control panel.

At 518, HMD 100 (and/or a device used to provide input at 516) can transmit instructions to server 204 that are indicative of input received at 516. In some embodiments, HMD 100 can transmit the instructions in any suitable format and/or using any suitable technique or combination of techniques.

At 520, server 204 can receive the instructions transmitted from HMD 100 to adjust a position of the instrument(s), and can determine an updated position for the instrument(s) based on the received instructions.

At 522, server 204 can generate an updated simulation based on the updated position of the instrument(s) using any suitable technique or combination of techniques. For example, server 204 can use techniques described above in connection with 506. Server 502 can return to 508, and can generate an updated visualization and/or instructions for rendering an updated visualization. Additional examples related to presenting interactive content to one or more users are described below in connection with FIG. 11.

Note that although only a single HMD 100 is shown in FIG. 5, server 204 can communicate with any suitable number of HMDs 100 that are participating in a simulation. Additionally, in some embodiments, server 204 can provide a visualization and/or information useable to render a visualization to devices other than HMDs (e.g., a user computing device associated with a 2D display, a cave automatic virtual environment associated with multiple projectors, etc.).

In some embodiments, process 500 can be used in a variety of applications. For example, process 500 can be used to collaboratively plan a cranial neurosurgical trajectory and/or placement (e.g., for a DBS probe, for SEEG electrodes, for a CED probe, for a LITT probe) using a 3D model of a patient-specific head and brain (e.g., MRI data, CT data).

FIG. 6 shows an example 600 of a process for generating a model useable to generate a biophysical simulation in accordance with some embodiments of the disclosed subject matter. In some embodiments, any suitable computing device can execute process 600, such as server 204. As shown in FIG. 6, at 602 process 600 can receive medical imaging data (e.g., MRI data, CT data, etc.) representing at least a portion of a subject's anatomy from any suitable source or sources. For example, process 600 can receive medical imaging data from a medical imaging device (e.g., an MRI scanner, a CT scanner). As another example, process 600 can receive medical imaging data from a server configured to store medical imaging data (e.g., a picture archiving and communication system (PACS) server). As yet another example, process 600 can receive medical imaging data from local storage (e.g., memory associated with a computing device executing process 600, such as memory 420 of server 204). As still another example, process 600 can receive medical imaging data from remote storage (e.g., from a cloud storage service, from a network attached storage device, etc.).

At 604, process 600 can generate a subject-specific anatomical model based on the received imaging data, a representative anatomical model, and/or one or more biophysical models that represent anatomical structures.

For example, as described below in connection with FIG. 7, process 600 can associate different portions of the medical imaging data with different anatomical structures, and biophysical models of the structure(s) (e.g., which can be used to simulate processes involving the structure(s)) can be associated with those portions of the medical imaging data.

At 606, process 600 can receive a selection of one or more instruments to be used in the simulation. For example, process 600 can receive a selection from an HMD or other computing device (e.g., user computing device 220) indicating an instrument(s) to be used in the simulation.

At 608, process 600 can receive a model of the selected instrument(s) from any suitable source or sources. For example, process 600 can receive the model of the selected instrument from local storage (e.g., memory associated with a computing device executing process 600, such as memory 420 of server 204). As another example, process 600 receive the model of the selected instrument from remote storage (e.g., from a cloud storage service, from a network attached storage device, etc.).

At 610, process 600 can place the instrument(s) in an initial position with respect to the subject-specific anatomical model. For example, process 600 can calculate an optimal trajectory based on a target anatomical structure and the subject's anatomy (e.g., received from a computing device, such as an HMD or other user computing device).

FIG. 7 shows an example 700 of a process for generating a subject-specific anatomical model in accordance with some embodiments of the disclosed subject matter. In some embodiments, any suitable computing device can execute process 600, such as server 204. As shown in FIG. 7, at 702, process 700 can convert medical imaging data into a particular format that can be used to associate the medical imaging data with particular anatomical structures. For example, medical imaging data (e.g., CT, MRI, etc.) that is in a digital imaging and communications in medicine (DICOM) format, can be converted to a neruoimaging informatics technology initiative (NIfTI) format. In a more particular example, process 700 can use a software tool, such as dem2nii, which can be obtained as part of MRI MRIcron software package.

In some embodiments, process 700 can coregister different images of a subject (e.g., from a particular study, such as a head and brain MRI study) to generate a 3D volume including multiple slices of medical imaging data. For example, process 700 can generate and/or use a preoperative surgical targeting T1-weighted (T1w) MRI to represent the anatomical foundation for the subject-specific anatomical model.

Figure 14:
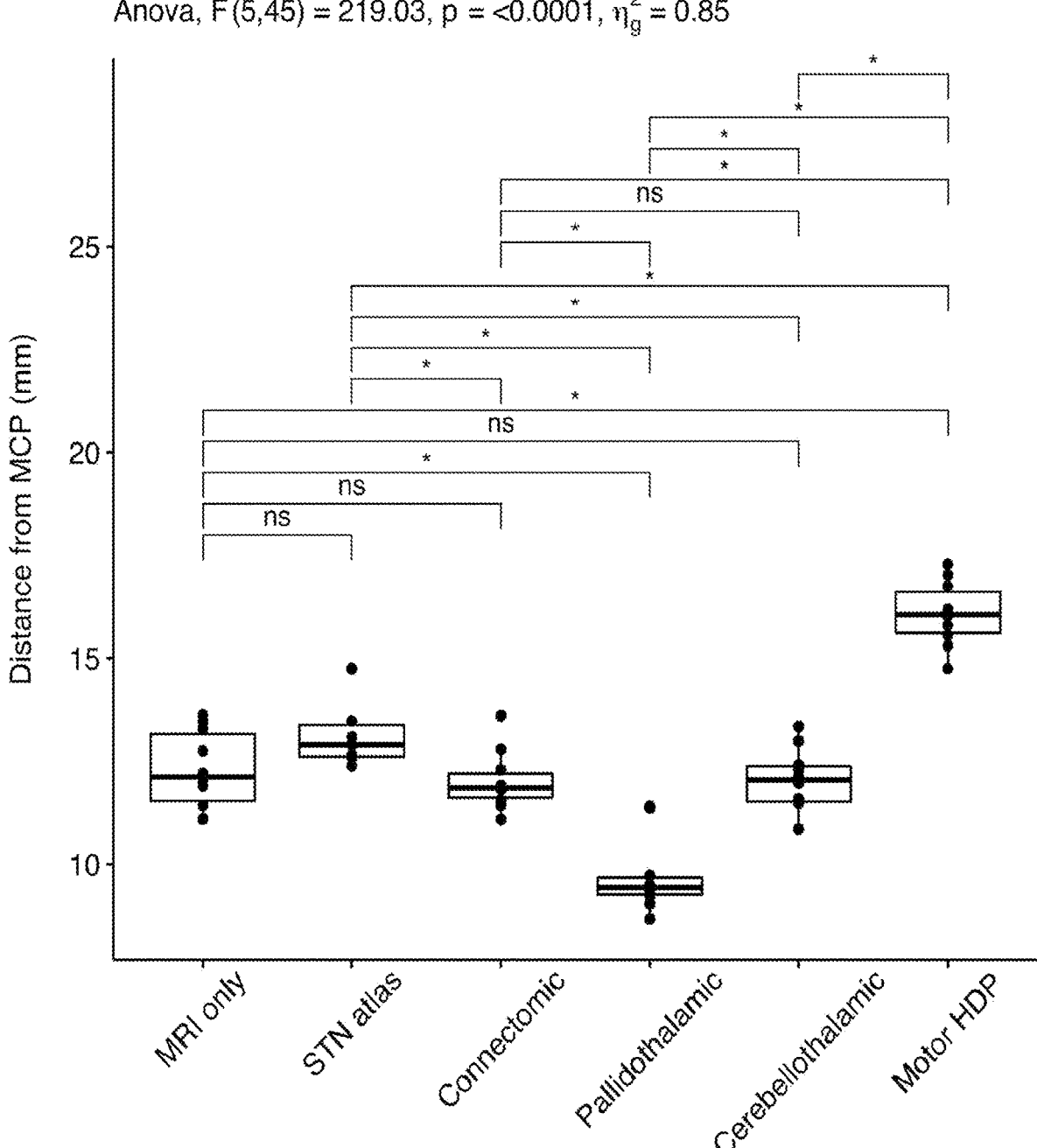
FIG. 14 shows an example statistical comparison of various DBS plans, including plans developed using conventional techniques, and a plan developed using mechanisms described herein.

In some embodiments, pre-operative medical imaging datasets used for surgical planning can be used as the foundation of each patient-specific model generated using mechanisms described herein. For example, such datasets can include T1-weighted (T1w) MRI data, T2-weighted (T2w) MRI data, and CT data. Results described below in connection with FIG. 14 are based on simulations generated using MRI data that was collected on a Siemens 3T MRI scanner with 3D T1w scans (1 mm slice thickness, 0.67 mm×0.67 mm pixel size) and 3D T2w scans (1 mm slice thickness, 0.5 mm×0.5 mm pixel size). The MRI image data was converted from DICOM to NIfTI format using MRIcron with the dcm2nii tool (e.g., available at neuro(dot)debian (dot)net/pkgs/mricron(dot)html). The data was then denoised, pixels corresponding to skull were removed (e.g., skull stripping was performed), and the images were bias corrected using Advanced Normalization Tools (ANTs) (e.g., available at pics1(dot)upenn(dot)edu/software/ants/), which facilitated rigid co-registration of data from different modalities. The T1w MRI was used as the base image for co-registration of the datasets. Pixels of the CT image corresponding to skull, and pixels of MRI data corresponding to ventricles and vessels, were segmented using Mimics (e.g., available at www(dot)materialize(dot)com/en/medi-cal/mimics-innovation-suite). Additionally, the pial surface of the brain was extracted from the MRI data using Free-surfer (e.g., available at surfer(dot)nmr.mgh.harvard.edu/).

At 704, process 700 can coregister the image data converted at 702 to an anatomical model (e.g., an atlas). For example, process 700 can coregister head and brain MRI data with a brain atlas (e.g., the CIT168 brain atlas developed at the California Institute of Technology) by using a nonlinear transformation matrix and warp field to map the structures represented by the atlas to the subject-specific MRI data. In a more particular example, the nonlinear transformation matrix and warp field can be generate using Advanced Normalization Tools (ANTs) made available from the University of Pennsylvania Image Computing & Science Lab. In such an example, the subject-specific T1w image data (e.g., in NIfTI format) is used as a fixed image, and the T1w image from the brain atlas is a moving image that is warped to more closely resemble the fixed image.

In some embodiments, process 700 can use predefined axonal pathways (e.g., anatomist defined pathways described in Petersen et al., "Holographic reconstruction of axonal pathways in the human brain," Neuron, 2019; 104: 1056-1064) within the CIT168 space, and can co-register the axonal pathways with the 3D volumes of 16 subcortical nuclei included in the CIT168 atlas brain. In some embodiments, the predefined axonal pathways can be grouped into various general pathways, such as: 1) subthalamopallidal, 2) pallidosubthalamic, 3) pallidothalamic, 4) cerebellotha-lamic, 5) medial lemniscus, 6) motor internal capsule (IC), 7) prefrontal cortex (PFC) IC, 8) motor hyperdirect, and 9) PFC hyperdirect. In some embodiments, each axonal pathway can include 50-250 individual streamlines that mimic anatomically defined 3D trajectories of the pathway (e.g., as shown in FIG. 10).

At 706, process 700 can apply the transformation matrix and warp field used to coregister the image data to the anatomical model at 704 to one or more biophysical models of an anatomical structure(s) to be modeled. For example, process 700 can apply the transformation matrix and warp field to representative biophysical models of the anatomical structures to cause the model to more closely conform to the expected position of the modeled anatomical structure in the subject. In a particular example, process 700 can apply the transformation matrix and warp field to polygonal data of 3D anatomical nuclei (e.g., described in Pauli et al., "A high-resolution probabilistic in vivo atlas of human subcortical brain nuclei," Sci Data 2018; 5; 180063) and axonal pathway streamlines (e.g., described in Petersen et al., "Holographic reconstruction of axonal pathways in the human brain," Neuron, 2019; 104:1056-1064), which can place the biophysical models into the subject-specific anatomical model.

In some embodiments, process 700 can co-register the CIT168 brain to the patient brain using a non-linear transformation matrix and warp field that is created via ANTs using symmetric normalization (SyN) (e.g., as described in Klein et al., "Evaluation of 14 nonlinear deformation algorithms applied to human brain MRI registration," NeuroImage, 46(3): 786-802 (2009)). For example, process 700 can use the patient's T1w image as a "fixed image" and the CIT168 T1w image as a "moving image." Process 700 can then apply the resulting transformation matrix and warp field to the polygonal data of the 3D anatomical nuclei and axonal pathway streamlines, which can place those model components into a patient-specific space.

In some embodiments, a patient-specific model generated using process 700 can include various data, such as: 1) T1w MRI, 2) T2w MRI, 3) CT, 4) skull, 5) pia, 6) vessels, 7) ventricles, 8) atlas nuclei, and 9) axonal pathways. In some embodiments, process 700 can then analyze the co-registered datasets to establish the AC-PC coordinate system, and when applicable, position the stereotactic frame model with the fiducial markers in the CT image (e.g., using techniques described in Coenen et al., "One-pass deep brain stimulation of dentato-rubro-thalamic tract and subthalamic nucleus for tremor-dominant or equivalent type Parkinson's disease," Acta Neurochir (Wien), 158(4):773-781 (2016)). In some embodiments, the co-registered and aligned imaging data, frame system, anatomical volumes, and axonal pathway models can be saves using any suitable format (e.g., as .png, .obj, .obj, .vtk file formats, respectively), for subsequent loading in connection with presentation of a holographic simulation of the patient (e.g., as described above in connection with FIG. 5).

FIG. 8 shows an example biophysical simulations that can be presented in an interactive mixed reality environment in accordance with some embodiments of the disclosed subject matter. FIG. 8, panel a1, shows a visualization of a patient-specific anatomical model that includes MRI data (shown as two intersecting orthogonal images), anatomical-nuclei (shown as 3D volumes of particular colors), a DBS probe, and a stereotactic frame coordinate system (shown by green fiducial markers). The nuclei position and size of the nuclei were determined using the CIT168 brain atlas, as described above in connection with process 700 of FIG. 7.

FIG. 8, panel a2, shows the visualization of FIG. 8, panel a1, with axonal pathway models included. The axonal pathway positions and trajectories were determined using the CIT168 brain atlas, as described above in connection with process 700 of FIG. 7.

FIG. 8, panel b1, shows a zoomed-in view of the subthalamic region with a BSN 2202 DBS lead placed in the subthalamic nucleus (STN) (shown as a green volume) and surrounded by the thalamus (shown as a yellow volume) and the globus pallidus (shown as a blue volume). In FIG. 8, panel b1, contact 5 of the DBS probe is active (which is shown by pink highlighting). FIG. 8, panel b2, shows the zoomed in view of FIG. 8, panel b1, with axonal pathway models included.

FIG. 8, panel c, shows the zoomed-in view of FIG. 8, panel b1, with basal ganglia pathways in shades of blue and green. More particularly, pallidothalamic pathways are shown in light blue, subthalamopallidal are shown in green, and pallidosubthalamic fibers are shown in dark blue.

FIG. 8, panel d, shows the zoomed-in view of FIG. 8, panel b1, with cerebellothalamic pathways shown in orange, and various corticofugal pathways, including internal capsule (IC) fibers of passage, with IC motor fibers shown in white, IC prefrontal cortex (PFC) shown in tan, and hyperdirect pathway (HDP), including HDP motor shown in pink, and HDP PFC shown in burnt orange.

Figure 9:
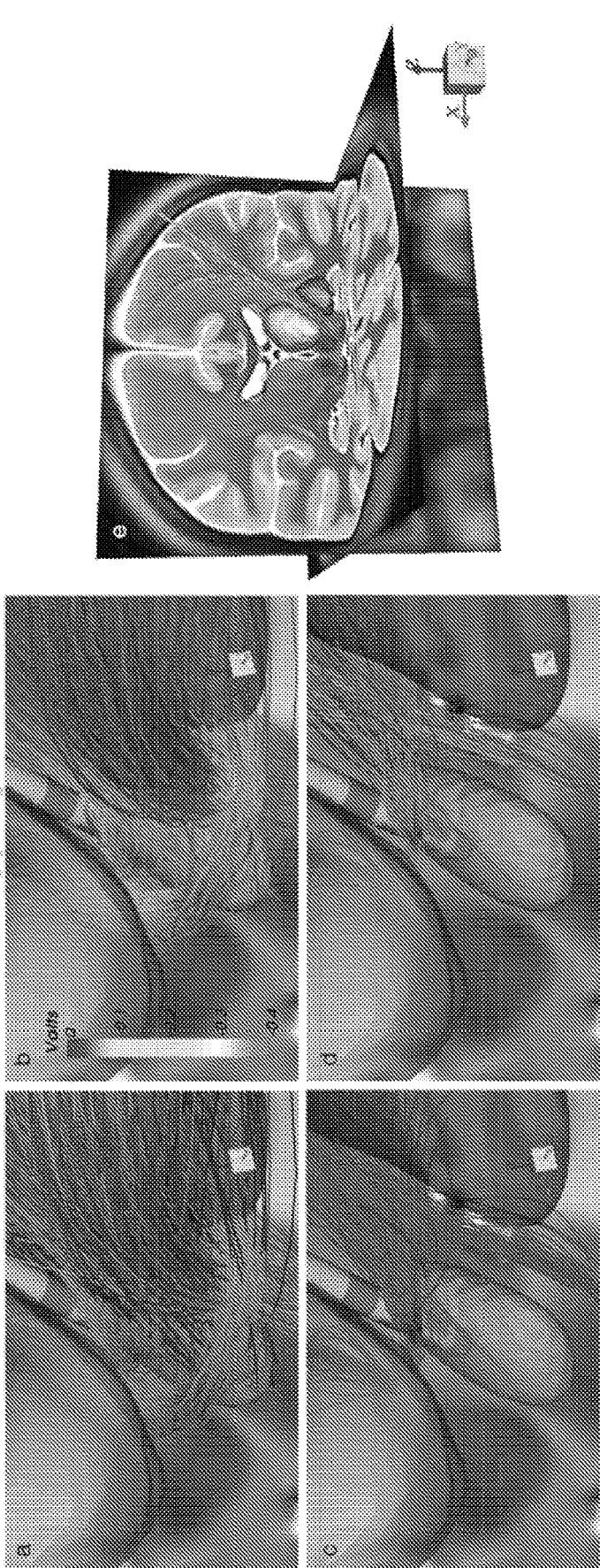
FIG. 9 shows another example of biophysical simulations that can be presented in an interactive mixed reality environment in accordance with some embodiments of the disclosed subject matter.

FIG. 9 shows another example biophysical simulations that can be presented in an interactive mixed reality environment in accordance with some embodiments of the disclosed subject matter. FIG. 9, panel a, shows the zoomed-in view of FIG. 8, panel b2, including axonal pathway models.

FIG. 9, panel b, shows a simulated extracellular voltage distribution applied to each axon model from −1 milliamp (mA) (cathodic) 60 microsecond (usec) stimulation delivered through contact 5 of the DBS probe.

FIG. 9, panel b, shows activated pathways in red, as calculated using the driving-force algorithm described in Howell et al., "A driving-force predictor for estimating pathway activation in patient-specific models of deep brain stimulation," Neuromodulation, 2019; 22:403-415. In FIG. 9, panel c, presentation of pathways that were not activated is inhibited.

FIG. 9, panel d, shows the activated pathways from FIG. 9, panel c, presented using color corresponding to anatomical pathway (e.g., as described above in connection with FIG. 8, panels c and d). FIG. 9, panel e, shows a whole-brain view including the activated connections with cortex.

FIG. 10 shows yet another example of biophysical simulations that can be presented in an interactive mixed reality environment in accordance with some embodiments of the disclosed subject matter.

In FIG. 10, a simulation of subthalamic deep brain stimulation (DBS) is shown. The data shown in FIG. 10 was derived from the CIT168 brain atlas. FIG. 10, panel (a) shows coronal and axial MRI data with 3D anatomical volumes representing the thalamus (yellow), STN (green), and globus pallidus (blue) shown, with a clinical DBS electrode (teal shaft) positioned in the model with a typical surgical trajectory and placement in the posterior STN. FIG. 10, panel (b) shows a zoom in on the subthalamic region. The pink electrode contact is in a representative location for typical therapeutic stimulation.

FIG. 10, panel (c) shows the visual of FIG. 10, panel (a) with some of the axonal pathways that course through the subthalamic region added to the visualization. For example, the following basal ganglia pathways are included in FIG. 10, panel (c): pallidothalamic (light blue), subthalamopallidal (green), pallidosubthalamic (dark blue). As another example, cerebellothalamic (orange) pathways are included in FIG. 10, panel (c). As another example, the following corticofugal pathways are included in FIG. 10, panel (c): internal capsule (IC) fibers of passage (white—motor IC; tan—PFC IC) and hyperdirect pathway (HDP) (pink—motor HDP; burnt orange—PFC HDP). FIG. 10, panel (d) shows a zoom in of the subthalamic region with the axonal pathways.

Deep brain stimulation (DBS) of the subthalamic region is an established treatment for the motor symptoms of Parkinson's disease (PD). However, the exact neural target(s) of the stimulation are still debated in the scientific literature. The subthalamic nucleus (STN) is the MRI-based targeting proxy that is typically used when planning surgery to implant a DBS probe (e.g., as shown in FIG. 10). The human STN is an approximately 150 mm$^3$ structure, and model-based estimates of the therapeutic stimulation volume are about 75 mm$^3$. The target location for stimulation is currently postulated to be biased toward the dorsal and posterior aspects of the STN. However, the STN is surrounded by many different axonal pathways, and stimulation of some of those pathways might be related to therapeutic benefit. As such, even after decades of clinical experience, wide-ranging clinical opinions exist on the best surgical placement location for subthalamic DBS electrodes. To complicate matters further, the surgical procedure itself is also associated with additional ambiguities. For example, stereotactic neurosurgical frames suffer from about 1 mm of mechanical error, and the brain can shift about 1 mm in the subthalamic region during the surgery. In turn, clinical results suggest that about 15% of implanted DBS leads are misplaced enough to justify a removal/revision surgery.

Efforts to understand the origin of the variance in clinical DBS electrode placement are complicated by the wide range of different strategies for image-based patient-specific DBS surgical planning. Mechanisms described herein were used to perform a head-to-head comparison of several different targeting strategies for subthalamic DBS, with goals of better understanding the neuroanatomical details associated with each strategy, and providing insight on how the nuances of the pre-operative planning process may bias the surgical result to different stimulation locations within the subthalamic region.

Additionally, mechanisms described herein were used to study developments in connectomic DBS modeling, which have introduced the concept of directly targeting axonal pathways in DBS surgical planning. Connectomic datasets often include complex 3D information on the axonal pathways, which can sometimes be difficult to interpret with traditional 2D software interfaces. In some embodiments, mechanisms described herein can be used to transition visualization of the surgical planning data out of the 2D computer screen and into a head mounted display (HMD) to facilitate 3D holographic visualization. Mechanisms described herein can be used to provide a new environment for DBS hypothesis development with interactive visualization of the patient anatomy, adjustment of the stereotactic frame, and positioning of the DBS electrodes, as it would be performed in the operating room. Additionally, in some embodiments, patient-specific models described herein can also incorporate recent advances in brain atlas anatomical volumes and axonal pathway models. As described below in connection with FIGS. 12-14, mechanisms described herein were used to create patient-specific DBS surgical plans with traditional "anatomic" nucleus targeting strategies, as well as new "connectomic" axonal pathway targeting strategies, and compared their differences within a population of PD patients.

FIG. 11 shows an example of a head mounted display that can be used in accordance with some embodiments of the disclosed subject matter, and examples of user interfaces that can be presented in an interactive mixed reality environment in accordance with some embodiments of the disclosed subject matter.

FIG. 11, panel (a) shows an example of a HoloLens 2 head mounted display (HMD) sold by Microsoft, Corp. FIG. 11, panel (b) shows an example of a wire frame hand avatar generated using hand tracking data generated by a HoloLens 2 device, which facilitates representation of a user's hand in the virtual space (blue hand). The tip of the virtual index finger can be used to adjust buttons and sliders on the holographic control panel shown in FIG. 11, panel (b).

FIG. 11, panel (c) shows arc and ring components of a stereotactic neurosurgical frame system (green) visualized with patient-specific imaging data generated using mechanisms described herein. Remote networking capabilities can enable users from distant locations to participate in the surgical planning. Head and hand, position, and orientation, for each remote user (blue avatar) can be visualized by each HMD.

FIG. 11, panel (d) shows a visualization of the transparent cortical surface, axonal pathways, anatomical nuclei, and MRI data. Colors for the anatomical nuclei and axonal pathways are the same as described above in connection with FIG. 10.

Mechanisms described herein can be implemented with any suitable extended reality device, such as a mixed reality device (e.g., HoloLens 2), a virtual reality device, etc. HoloLens 2 is an untethered HMD that uses see transparent screens and stereoscopic rendering to generate a visual scene that the user interprets as a 3D hologram. In some embodiments, mechanisms described herein can be implemented for use with a mixed reality device using a 3D rendering platform. For example, the visualizations shown in FIGS. 10-13 were generated using an implementation developed using the Unity Game Engine and the Mixed Reality Toolkit from Microsoft.

Figure 12:
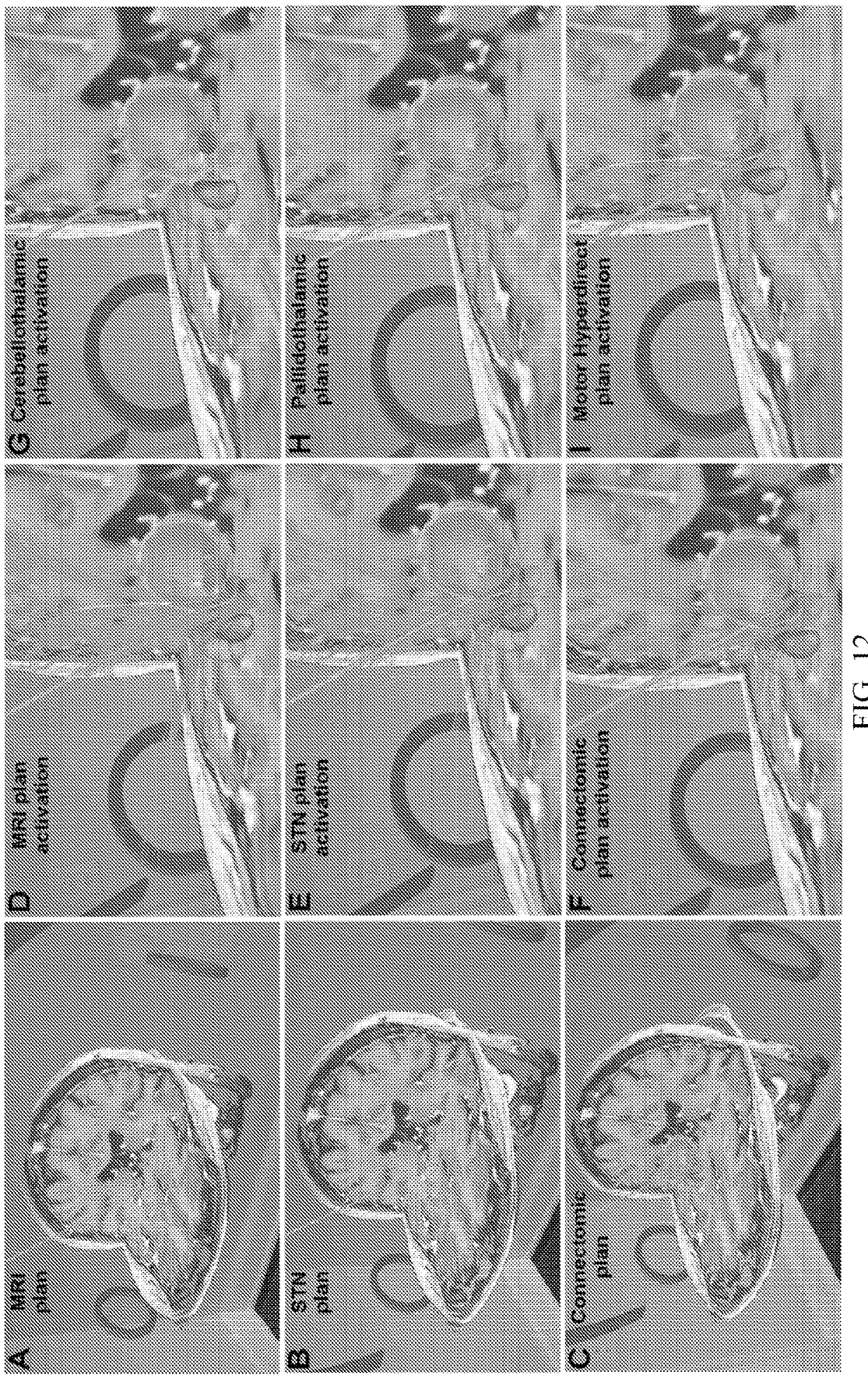
FIG. 12 shows examples of various DBS surgical plans presented using mechanisms described herein, including plans developed using conventional techniques, and a plan developed using mechanisms described herein.

FIG. 12 shows examples of various DBS surgical plans presented using mechanisms described herein, including plans developed using conventional techniques, and a plan developed using mechanisms described herein.

FIG. 12, panel (a) shows a surgeon-defined MRI only plan. Intended to mimic the current clinical standard where the target point for contact 1 of a DBS probe was defined based on inspection of the patient-specific MRI data. FIG. 12, panel (b) shows a surgeon-defined STN atlas plan. The surgeon was instructed to place contact 1 of the DBS probe in the posterior STN volume. The STN volume was defined by non-linear warp of the CIT168 brain atlas to the patient-specific MRI data (e.g., as described above in connection with process 700 of FIG. 7).

FIG. 12, panel (c) shows a surgeon-defined connectomic plan. The surgeon was instructed to place contact 1 of the DBS probe such that activation of putative therapeutic pathways were maximized and activation of putative side-effect pathways were minimized. FIG. 12, panels (d), (e), and (f) show pathway activation generated by the different surgeon-defined plans, and FIG. 12, panels (g), (h), and (i) show pathway activation generated by the model-defined pathway selective plans. Colors for the anatomical nuclei and axonal pathways are the same as described above in connection with FIG. 10.

FIG. 13 shows examples of electrode placements based on various DBS surgical plans presented using mechanisms described herein.

An example patient with each surgical plan denoted by a different color electrode shaft in FIG. 13, panels (a) and (b), which show the same visualization from two different angles, specifically panel (a) shows a coronal view, and panel (b) shows a sagittal view. The DBS probes are color coded as follows: MRI only plan—white, STN atlas plan—green, Connectomic plan—dark blue, Pallidothalamic plan—light blue, Cerebellothalamic plan—orange, Motor HDP plan—pink. Contact 1 for each lead is dark pink.

DBS surgical planning is typically performed using anatomical landmarks visible in the patient MRI as targeting proxies (e.g., the STN is used as a targeting proxy for subthalamic DBS). However, connectomic DBS is a burgeoning sub-field of research that uses model-based representations of the structural connectivity (e.g., axonal pathway models) to develop hypotheses on the neural targets of the stimulation. Mechanisms described herein were used to compare surgical plans created using traditional "anatomic" or "radiographic" targeting strategies with plans created using new "connectomic" targeting strategies, as described above in connection with FIGS. 12 and 13.

An experiment was performed in which 10 brain hemispheres from subjects that had PD were analyzed. These patients were recently implanted with subthalamic DBS using standard clinical practice. Internal review board (IRB) approval was obtained to reuse pre-operative MRI datasets to define new sets of DBS surgical plans using mechanisms described herein. For each brain hemisphere analyzed, 3 plans were created by an experienced DBS neurosurgeon, and 3 other plans were created by a computer algorithm. Each planning strategy was characterized by a different goal, which coincided with a different strategy on the best way to select a target point in the subthalamic region for DBS therapy for PD. The neurosurgeon-defined plans were: 1) MRI only, 2) STN atlas, and 3) Connectomic. The model-defined plans were: 1) Pallidothalamic, 2) Cerebellothalamic, and 3) Motor Hyperdirect Pathway (HDP). Each surgical plan was defined independently using mechanisms described herein to visualize patient data and relied on the use of different datasets that were available in each patient-specific model.

For the MRI only plan, the surgeon used the grey scale values in the Tlw and T2w MRI slices to identify a target point for the placement of contact 1 of a Medtronic 3389 DBS lead. The MRI only plan was performed first in each hemisphere studied. This plan was intended to mimic the traditional subthalamic DBS planning process performed in standard clinical practice. An initial target area was estimated based on AC-PC coordinates and the location of the red nucleus. The surgeon then identified a specific voxel in the MRI that corresponded with the surgeon's estimate of the clinical target point for subthalamic DBS. This plan also included defining the burr hole location on the skull, entry point on a cortical gyrus, avoidance of vessels, and avoidance of ventricles. However, target definition for this plan only used stereotactic coordinates and the MRI data, and did not consider the brain atlas nuclei volumes or axonal pathway models.

The STN atlas volume plan was defined second in each hemisphere studied. The anatomical nuclei models were turned on, and the surgeon was instructed to use the 3D volume of the STN that was warped into patient space to define the target point. The stated goal was to position contact 1 of the DBS probe in the center of the posterior half of the STN atlas volume. This plan used only the MRI data and the STN atlas volume for target definition, and did not consider the axonal pathway models.

The connectomic plan was defined third in each hemisphere studied. For this plan, the surgeon was provided with the additional capabilities described herein, which included interactive use of all of the MRI datasets, anatomical volumes, axonal pathway models, and DBS activation volumes for visualization. The stated goal was to position the electrode such that a 2.5 mm radius activation volume surrounding contact 1 generated balanced stimulation of axonal pathways that were considered therapeutic, while avoiding pathways that were associated with side effects. The therapeutic pathways were defined as the pallidothalamic, subthalamopallidal, pallidosubthalamic, cerebellothalamic, and motor HDP. The pathways that were defined to be associated with side-effects were the medial lemniscus, motor IC, PFC IC, and PFC HDP. The surgeon interactively moved the electrode around the subthalamic region while being able to see the axonal pathway activation associated with the stimulation volume at contact 1 of the DBS probe. The surgeon then selected an electrode position that represented the surgeon's definition of an optimal connectomic plan, given the above listed instructions for this plan.

Three examples of model-defined pathway-specific plans were also created with a computer algorithm and were only Each of the six different planning strategies resulted in a different target point for subthalamic DBS in each of the ten brain hemispheres studied (see, e.g., FIG. 13). These different target points spanned several millimeters in every direction, and resulted in different predictions on the axonal pathway activation from DBS (see FIG. 12 and TABLE 1, below). Electrode locations that were near the center of the STN (e.g., MRI only and STN atlas plans) generally activated a wide range of pathways, typically including a combination of motor HDP, pallidosubthalamic, and subthalamopallidal pathways. Electrode locations that were dorsal and medial to the center of the STN (e.g., Pallidothalamic plan) typically exhibited strong activation of the pallidothalamic pathway, with limited activation of the other pathways. Electrode locations that were dorsal and posterior to the center of the STN (e.g., Connectomic plan) generally activated a wide range of pathways, typically including a combination of the motor HDP, pallidothalamic, and cerebellothalamic pathways. Electrode locations that were posterior to the center of the STN (e.g., Cerebellothalamic plan) typically exhibited strong activation of the cerebellothalamic pathway, with limited activation of the other pathways. Electrode locations that were posterior and lateral to the center of the STN (e.g., Motor HDP plan) typically exhibited moderate activation of the motor HDP, with limited activation of the other pathways.

TABLE 1

| Target * coordinates | MRI only | STN atlas | Connectomic | Pallidothalamic | Cerebellothalamic | Motor HDP |
|---|---|---|---|---|---|---|
| X (lateral) | −11.1 ± 1.1 | −11.6 ± 1.1 | −10.3 ± 0.6 | −8.6 ± 1.1 | −10.2 ± 1.2 | −14.4 ± 1.0 |
| Y (posterior) | −3.4 ± 0.3 | −3.6 ± 0.6 | −3.7 ± 0.5 | −1.9 ± 0.9 | −5.2 ± 1.2 | −5.4 ± 0.9 |
| Z (ventral) | −4.2 ± 0.4 | −5.4 ± 0.9 | −4.0 ± 0.8 | −2.9 ± 1.3 | −3.1 ± 1.7 | −3.6 ± 2.4 |
| Pathway ** activation (%) | | | | | | |
| Pallidothalamic | 14.9 ± 15.1 | 0.1 ± 0.1 | 14.2 ± 7.6 | 100.0 ± 0.1 | 1.2 ± 2.9 | 0.0 ± 0.0 |
| Cerebellothalamic | 35.7 ± 39.7 | 9.1 ± 12.8 | 67.9 ± 26.1 | 1.7 ± 2.8 | 100.0 ± 0.0 | 0.7 ± 0.7 |
| Pallidosubthalamic | 31.6 ± 9.1 | 38.3 ± 3.8 | 23.0 ± 4.0 | 5.5 ± 2.5 | 2.9 ± 3.1 | 9.2 ± 0.6 |
| Subthalamopallidal | 32.7 ± 10.4 | 38.6 ± 3.4 | 22.8 ± 4.2 | 6.1 ± 2.7 | 2.4 ± 2.6 | 8.0 ± 1.3 |
| Motor IC | 0.0 ± 0.1 | 0.7 ± 1.1 | 0.0 ± 0.0 | 0.0 ± 0.0 | 0.0 ± 0.0 | 5.9 ± 3.2 |
| Motor HDP | 53.2 ± 15.0 | 72.5 ± 4.8 | 37.6 ± 6.8 | 6.2 ± 2.9 | 5.3 ± 3.9 | 20.4 ± 1.4 |
| Prefrontal IC | 0.0 ± 0.0 | 0.0 ± 0.0 | 0.0 ± 0.0 | 0.0 ± 0.0 | 0.0 ± 0.0 | 0.0 ± 0.0 |
| Prefrontal HDP | 6.8 ± 4.3 | 14.0 ± 1.9 | 3.1 ± 1.3 | 0.8 ± 1.1 | 0.5 ± 0.6 | 1.7 ± 3.5 |

* Relative to the left hemisphere, measured from the MCP; Average arc angle ± 19.1° ± 1.3 from the mid-sagittal plane; Average ring angle = 64.2° ± 6.4 from the AC-PC plane.
** Percentage of fibers in a given pathway coursing through a 2.5 mm radius activation volume at contact 1.

shown to the surgeon after the surgeon generated plans using techniques described above. The algorithm defined a target point in the subthalamic region that optimized the overlap of the 2.5 mm radius contact 1 activation volume with the specified target pathway (e.g., cerebellothalamic, pallidothalamic, or motor HDP). The optimization relied on a cost function that maximized activation of the target pathway, while first minimizing overlap with the side-effect pathways, and then second minimizing overlap with any other therapeutic pathways. As such, the model-defined plans provided a theoretical optimum for selective DBS of the targeted pathway within the context of the pre-operative imaging data used for each patient-specific HoloDBS model.

Mechanisms described herein were then used to evaluate different planning approaches to subthalamic DBS surgical targeting, with a goal to compare surgical plans generated by traditional "anatomic" or "radiographic" DBS targeting strategies (e.g., MRI only or STN atlas plans), with plans generated by new "connectomic" DBS targeting strategies (e.g., Connectomic, Pallidothalamic, Cerebellothalamic, or Motor HDP plans), all within the same PD patients. Six total surgical plans were created for each brain hemisphere.

The results show a significant effect of targeting strategy on the measured distance of the target point (centroid of contact 1) to the MCP (F(5, 45)=219.035, p<0.001, generalized eta squared=0.850) (see, FIG. 14). Bonferroni-corrected pairwise comparisons revealed that the "MRI only" strategy yielded significantly different distances than the "Pallidothalamic" and the "Motor HDP" strategies (p<0.001) while being statistically comparable to the "STN atlas", "Cerebellothalamic", and "Connectomic" strategies (p>0.05). The "STN atlas" strategy significantly differed from the "Connectomic", "Pallidothalamic", "Cerebellothalamic", and "Motor HDP" strategies (p<0.001). The "Connectomic" strategy was significantly different from the "Pallidothalamic", "Motor HDP", and "STN atlas" strategies (p<0.001), while being statistically similar to the "Cerebellothalamic" and "MRI only" strategy (p>0.05). The "Pallidothalamic" and "Motor HDP" strategies were different from all other strategies (p<0.001).

The results suggest that the different planning strategies generate different target points in the subthalamic region. However, it remains unclear how stimulation at those different target points might affect clinical outcome. Mechanisms described herein can play a useful role in facilitating future clinical investigations into those fundamental questions for the field of DBS.

In some embodiments, mechanisms described herein can be used to create an interactive holographic visualization tools for stereotactic neurosurgery research. Additionally, mechanisms described herein can leverage the large assortment of 3D datasets that are used in neurosurgical planning, and can mitigate the complexity of defining a safe trajectory through the brain to reach a target point. There is also a growing clinical interest in integrating the latest scientific advances in 3D anatomical models of brain nuclei and axonal pathway models into the DBS surgical planning process. However, facilitating visual integration, and establishing functional utility, for all of the different 3D datasets within a traditional 2D screen-based software interface can be challenging. Mechanisms described herein can provide an environment where all of the pertinent information for a patient-specific DBS surgical plan can be interactively visualized as a 3D hologram. Additionally, mechanisms described herein can be used to network multiple HMDs together to facilitate local and/or remote collaborative interactions.

In some embodiments, mechanisms described herein can be used to present integrated holographic multi-modal data, and can be especially useful for trajectory planning. The specific results presented in connection with FIGS. 12-14 are focused on target point definition within the subthalamic region, but an equally important clinical step of DBS surgical planning is the definition of a safe trajectory to that target. The ability to visualize all of the relevant anatomical structures (e.g., skull, cortex, vessels, ventricles, etc.) in 3D, with the ability to interactively adjust the arc and ring angles of the electrode trajectory, simplifies the mental integration that is needed for trajectory planning. Scores of different stereotactic neurosurgeons have participated demonstrations of a software tool that implements mechanisms described herein and have considered this feature a major highlight of the tool. Additionally, while the specific utility of holographic visualization is difficult to quantify with an individual metric, the instantaneous mental fusing of spatially complex 3D datasets is undeniable when using technology that implements mechanisms described herein.

Another important takeaway from demonstrations to the clinical community has been the substantial diversity of opinions on the underlying anatomical target of subthalamic stimulation. In reality, the optimal therapeutic target point for subthalamic DBS is unknown, and it is possible that the concept of a single target point is a theoretical fallacy. The anatomy, physiology, and symptom profile of each PD patient is unique, and hence their optimal location for stimulation may also be unique. The basic question of pre-operative target definition was presented as an interesting example of the kinds of research analyses that can be performed using mechanisms described herein.

Results described herein show that the target points associated with different subthalamic DBS planning strategies are significantly different. Interestingly, the surgeon-defined MRI only, STN atlas, and Connectomic plans were similar from a geometric perspective, which reinforces the general clinical finding that the dorsal STN area is typically associated with therapeutic benefit from subthalamic DBS. Those three different plans also exhibited co-activation of several different axonal pathways, albeit with varying ratios (see, e.g., FIG. 12, panels (d), (e), and (f), and TABLE 1), which highlights the wide range of pathways that course through that focal area. The model-defined pathway-specific plans exhibited greater geometric differences in their target points, which corresponded with more dramatic differences in their respective pathway activation simulations (see, e.g., FIG. 12 panels (g), (h), and (i) and TABLE 1). The distances separating the pathway-specific target points are large enough to suggest that prospective clinical trials could be designed to compare those strategies, as well as their therapeutic outcomes and side effect profiles. For example, tremor-dominant PD patients could be assigned to a Cerebellothalamic plan, while rigidity-dominant PD patients could be assigned to a Pallidothalamic plan. This would provide an opportunity to more selectively stimulate a specific pathway that is hypothesized to be linked to a specific symptom, which could help elucidate structure-function relationships for the brain circuitry in the subthalamic region.

Extensive validation testing of the coordinate systems and data co-registration processes described herein have been carried out. Additionally, the explicit accuracy of the presented data is equivalent when seen as a hologram or on a 2D computer screen. Currently available techniques for co-registering different data sets may limit the accuracy of visualizations generated using mechanisms described herein. For example, ANTs was used to co-register imaging datasets prior to loading them into software that implements mechanisms described herein. While this can be expected to be the most accurate approach currently available, an estimated registration error of about 1 mm is still estimated between the various datasets. Improved co-registration techniques can improve the accuracy of visualizations generated using mechanisms described herein.

There are many different anatomical atlases, connectomic datasets, and DBS modeling strategies available in the literature. The optimal combination of datasets and strategies is unknown and likely dependent on the specific details of the analysis being performed. Accordingly, mechanisms described herein can be implemented to be agnostic to the datasets that are loaded into the system, and can be configured to be capable of accommodating new models as they become available.

Additionally, visualization capabilities of currently available HMDs may limit the accuracy of the visualizations, which can be improved with improved visualization hardware. For example, the waveguide in HoloLens 2 provides a 52 degree field of view to the user with 1440×936 pixel per eye resolution. This can create a "cropped" view of the data, depending on the position of the user relative to the holographic simulation. However, users can simply adjust their position (and/or scale the hologram) to better visualize the scene, and in demonstrations many users naturally adapted to the field of view constraints after a few minutes of experience with the HMD.

Note that the most simplistic model of stimulation spread was used to generate the pathway activation simulations (e.g., a 2.5 mm radius sphere). This simplification enabled real-time interactive visualization of the connectomic targeting results as a user adjusted the electrode position, which was deemed more important than quantitative accuracy for this application. As such, the pathway activation estimates described herein (e.g., in TABLE 1) are gross approximations, but the trends are representative of results generated with scientifically detailed models of subthalamic DBS.

Result described herein demonstrate that substantial variance exists between different strategies for the important planning step of the DBS surgical process.

Hundreds of previous studies have already attempted to define correlations between retrospectively defined stimulation locations and behavioral outcomes from subthalamic DBS. However, one could argue that those retrospective studies have done little to answer key scientific questions or resolve clinical controversies on best practices. Alternatively, attempts to refine understanding of stimulation within a given brain region should first employ a well-defined pre-operative surgical targeting hypothesis associated with the specific question being explored. Results from that kind of study can be especially impactful, but such studies are unfortunately rare in DBS research. Accordingly, mechanisms described herein can aid in the prospective clinical testing of novel targeting hypotheses at the patient-specific level, and can expand the anatomical detail available for clinical decision making prior to those cases. Future results using tools implemented in accordance with mechanisms described herein can help improve understanding of the actual neural target(s) associated with therapeutic benefit from DBS.

FIG. 14 shows an example statistical comparison of various DBS plans, including plans developed using conventional techniques, and a plan developed using mechanisms described herein.

In particular, FIG. 14 shows statistical comparisons of DBS surgical plans, where target points are given relative to the mid-commissural point (MCP), ns indicates a statistically non-significant result, and * indicates a statistically significant result with $p<0.05$, Bonferroni-corrected.

Repeated-measures ANOVA were carried out to test the effect of using different DBS targeting methods (6 levels) on the target point (x,y,z) relative to the mid commissural point (MCP) (0,0,0). This measurement was simply calculated as the Euclidean distance between the points within the patient-specific imaging data. A target point (centroid of contact 1) was defined for each of the 6 different targeting methods, which were each obtained from the 10 different brain hemispheres.

Figure 15:
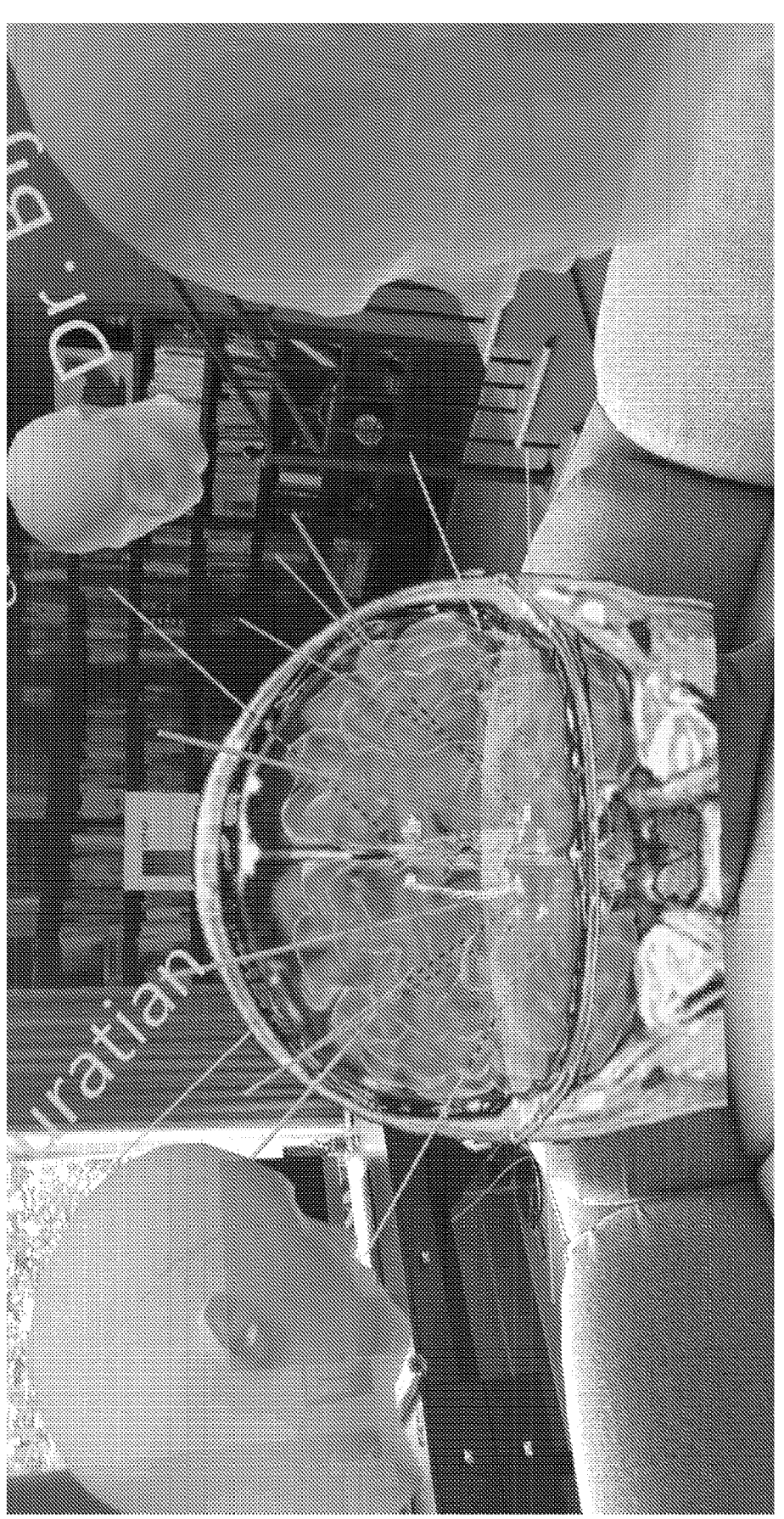
FIGS. 15A and 15B show examples of a biophysical simulation that can be presented in an interactive mixed reality environment in accordance with some embodiments of the disclosed subject matter.
Figure 16:
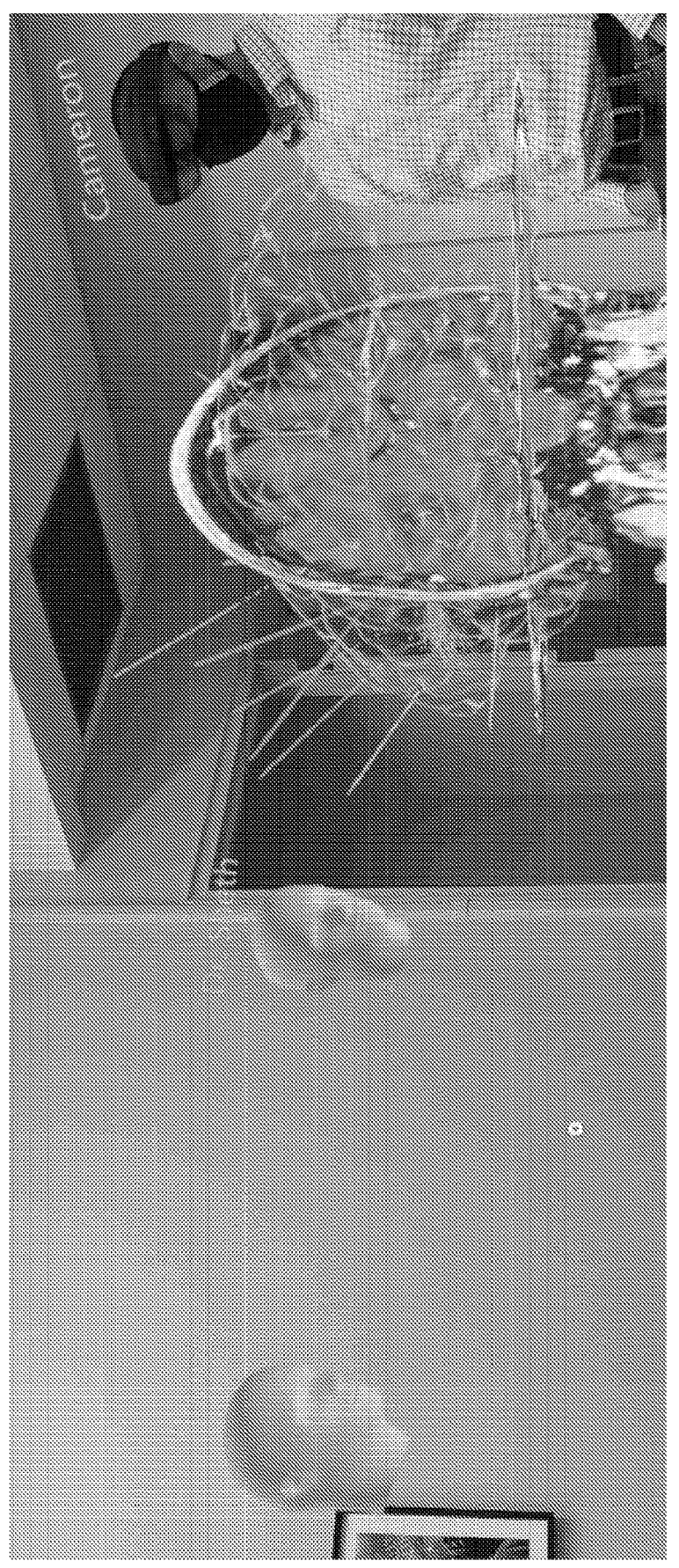

FIGS. 15A and 15B show examples of a biophysical simulation that can be presented in an interactive mixed reality environment in accordance with some embodiments of the disclosed subject matter. More particularly, FIG. 15A shows an example of a holographic simulation as presented by a first HMD that is being used to collaboratively plan placement of stereo-encephalography (SEEG) electrodes and DBS probe in the same brain, and FIG. 15B shows the same holographic simulation as presented by a second HMD at a different point in time. As shown in FIGS. 15A and 15B, remote users can be represented using avatars that are positioned relative to the simulation based on the orientation of the holographic simulation being presented by that user's HMD. For example, information indicative of a remote user's position and orientation relative to the holographic simulation can be provided to an HMD presenting the holographic simulation shown in FIGS. 15A and 15B, and the HMD can use the information to present an avatar (e.g., labeled with a semantically meaningful identifier, such as the remote user's name) associated with a remote user. This can facilitate collaboration by allowing remotely located users to better understand which part of the holographic simulation the remote user is currently viewing. In the example of FIGS. 15A and 15B four of the probes are DBS probes and ten probes are SEEG electrodes.

Further Examples Having a Variety of Features

Implementation examples are described in the following numbered clauses:

1: A method for presenting biophysical simulations in an interactive mixed reality environment, comprising: receiving medical imaging data associated with a subject; receiving, from a server, information useable to visualize a simulation of one or more biophysical processes in connection with a subject-specific anatomical model based on the medical imaging data; causing a visualization of the simulation to be presented, via a transparent display, in connection with the medical imaging data with an instrument presented in a first position; receiving, from the server, updated information useable to visualize an updated simulation of the one or more biophysical processes with the instrument in a second position; and causing a visualization of the updated simulation to be presented, via a transparent display, in connection with the medical imaging data with the instrument presented in the second position.

2. The method of clause 1, wherein the medical imaging data comprises T1-weighted magnetic resonance imaging (MRI) data that includes data corresponding to at least a portion of the subject's brain tissue.

3. The method of clause 1, wherein the medical imaging data comprises T2-weighted magnetic resonance imaging (MRI) data that includes data corresponding to at least a portion of the subject's brain tissue.

4. The method of clause 1, wherein the visualization includes a representation of the instrument. 5. The method of any of clauses 1 to 4, wherein the instrument is a deep brain stimulation (DBS) electrode comprising multiple electrode contacts.

6. The method of clause 5, further comprising: receiving, via an input device, input to manipulate an activation state of one or more of the contacts of the DBS electrode.

7. The method of any one of clauses 1 to 4, wherein the instrument comprises a stereo-encephalography (SEEG) electrode.

8. The method of any one of clauses 1 to 4, wherein the instrument comprises a convection enhanced delivery (CED) probe.

9. The method of any one of clauses 1 to 4, wherein the instrument comprises a laser interstitial thermal therapy (LITT) probe.

10. The method of any one of clauses 1 to 9, further comprising: receiving, via an input device, input to manipulate a position of the instrument; and transmitting, to the server, instructions based on the input.

11. The method of one of clause 10, further comprising receiving, from a sensor of a head mounted display, information indicative of a position of an index finger of a wearer of the head mounted display, wherein the input to manipulate the position of the instrument comprises movement of the index finger from a first position to a second position.

12. The method of any one of clauses 1 to 11, further comprising: transmitting, to the server, instructions to adjust a position of the instrument to the second position.

13. The method of any one of clauses 1 to 12, further comprising: receiving, via an input device, input to manipulate a position of a portion of the subject-specific anatomical model.

14. The method of any one of clauses 1 to 13, further comprising: transmitting, to the server, instructions to adjust a position of a portion of the subject-specific anatomical model.

15. The method of any one of clauses 1 to 14, wherein the at least one processor is further programmed to: receiving, via an input device, input to change a portion of the simulation that is visualized.

16. The method of any one of clauses 1 to 15, wherein the at least one processor is further programmed to: transmitting, to the server, instructions to change a portion of the simulation that is visualized.

17. A method for presenting biophysical simulations in an interactive mixed reality environment, comprising: receiving a selection of medical imaging data associated with a subject; generating a subject-specific anatomical model based on the medical imaging data; generating a simulation of one or more biophysical processes based on the subject-specific anatomical model and a first position of at least one instrument; generating information useable to visualize the simulation; transmitting the information useable to visualize the simulation to a plurality of head-mounted displays (HMDs); receiving, from a first HMD of the plurality of HMDs, an instruction to adjust a position of the instrument to a second position; generating an updated simulation of the one or more biophysical processes based on the subject-specific anatomical model and the second position of at least one instrument; generating information useable to visualize the updated simulation; and transmitting the information useable to visualize the updated simulation to the plurality of head-mounted displays.

18. The method of clause 17, wherein the medical imaging data comprises T1-weighted magnetic resonance imaging (MRI) data that includes data corresponding to at least a portion of the subject's brain tissue.

19. The method of clause 17, wherein the medical imaging data comprises T2-weighted MRI data that includes data corresponding to at least a portion of the subject's brain tissue.

20. The method of clause 17, wherein the visualization includes a representation of the instrument.

21. The method of any one of clauses 17 to 19, wherein the instrument is a deep brain stimulation (DBS) electrode comprising multiple electrode contacts.

22. The method of clause 21, wherein the at least one processor is further programmed to: receive, from the first HMD, instructions to manipulate an activation state of one or more of the contacts of the DBS electrode.

23. The method of any one of clauses 17 to 19, wherein the instrument comprises a stereo-encephalography (SEEG) electrode.

24. The method of any one of clauses 17 to 19, wherein the instrument comprises a convection enhanced delivery (CED) probe.

25. The method of any one of clauses 17 to 19, wherein the instrument comprises a laser interstitial thermal therapy (LITT) probe.

26. The method of any one of clauses 17 to 25, wherein the at least one processor is further programmed to: receive, from the first HMD, instructions to manipulate a position of a portion of the subject-specific anatomical model.

27. The method of any one of clauses 17 to 25, wherein the at least one processor is further programmed to: receive, from a device associated with the first HMD, instructions to adjust a position of a portion of the subject-specific anatomical model.

28. The method of any one of clauses 17 to 26, wherein the at least one processor is further programmed to: receive, from an HMD, instructions to change a portion of the updated simulation that is visualized; and generate updated information useable to visualize the updated simulation based on the instructions to change a portion of the updated simulation that is visualized; and transmit the updated information useable to visualize the updated simulation to the plurality of head-mounted displays.

29. The method of any one of clauses 17 to 27, wherein the at least one processor is further programmed to: receive, from a device associated with the first HMD, instructions to change a portion of the updated simulation that is visualized.

30. The method of any one of clauses 17 to 28, wherein the at least one processor is further programmed to: associate a portion of the medical imaging data with an anatomical structure; associate a biophysical model of the anatomical structure with the portion of the subject-specific anatomical model.

31. The method of clause 30, wherein the at least one processor is further programmed to: use a nonlinear transformation matrix and a warp field to associate a portion of a representative anatomical model with the portion of the medical imaging data; and use the nonlinear transformation matrix and a warp field to adjust a shape of the biophysical model of the anatomical structure.

32. The method of clause 31, wherein the representative anatomical model is a probabilistic brain atlas.

33. The method of clause 32, wherein the biophysical model of the anatomical structure is an axonal pathway.

34. The method of clause 33, wherein the at least one processor is further programmed to: convert the medical imaging data from a first format into a second format.

35. The method of clause 34, wherein the first format is a digital imaging and communications in medicine (DICOM) format.

36. The method of clause 35, wherein the second format is a neruoimaging informatics technology initiative (NIfTI) format.

37. A system comprising: at least one hardware processor that is programmed to: perform a method of any of clauses 1 to 34.

36. A non-transitory computer readable medium containing computer executable instructions that, when executed by a processor, cause the processor to perform a method of any of clauses 1 to 37.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any other suitable media that is fleeting and devoid of any semblance of permanence during transmission, and/or any suitable intangible media.

It will be appreciated by those skilled in the art that while the disclosed subject matter has been described above in connection with particular embodiments and examples, the invention is not necessarily so limited, and that numerous other embodiments, examples, uses, modifications and departures from the embodiments, examples and uses are intended to be encompassed by the claims attached hereto.

The entire disclosure of each patent and publication cited herein is hereby incorporated by reference, as if each such patent or publication were individually incorporated by reference herein.

Various features and advantages of the invention are set forth in the following claims.

The invention claimed is:

1. A system for presenting biophysical simulations in an interactive mixed reality environment, comprising:
    a head mounted display comprising:
        a transparent display;
        a plurality of sensors; and
        at least one processor, wherein the at least one processor is programmed to:
            receive medical imaging data associated with a subject, the medical imaging data comprising T1-weighted magnetic resonance imaging (MRI) data, T2-weighted MRI data, or computed tomography (CT) data corresponding to the subject's brain tissue;
            receive, from a server, information useable to visualize a simulation of one or more biophysical processes associated with the subject in connection with a subject-specific anatomical model associated with the subject based on the medical imaging data with an instrument in a first position, wherein the server generates the subject-specific anatomical model based on the medical imaging data by using a nonlinear transformation matrix and a warp field with an anatomical atlas;
            cause a visualization of the simulation to be presented, via the transparent display, in connection with the medical imaging data with the instrument presented in the first position;
            receive, from the server, updated information useable to visualize an updated simulation of the one or more biophysical processes in connection with the subject-specific anatomical model based on the medical imaging data with the instrument in a second position; and
            cause a visualization of the updated simulation to be presented, via the transparent display, in connection with the medical imaging data with the instrument presented in the second position.

2. The system of claim 1, wherein the visualization includes a representation of the instrument.

3. The system of claim 1, wherein the instrument is a deep brain stimulation (DBS) electrode comprising multiple electrode contacts.

4. The system of claim 3, wherein the at least one processor is further programmed to:
    receive, via an input device, input to manipulate an activation state of one or more of the contacts of the DBS electrode.

5. The system of claim 1, wherein the instrument comprises;
    a stereo-encephalography (SEEG) electrode;
    a convection enhanced delivery (CED) probe; or
    a laser interstitial thermal therapy (LITT) probe.

6. The system of claim 1, wherein the at least one processor is further programmed to:
    receive, via an input device, input to manipulate a position of the instrument; and
    transmit, to the server, instructions based on the input.

7. The system of claim 6, wherein:
    the head mounted display further comprises the input device;

the input device comprises a sensor; and
the at least one processor is further programmed to:
    receive, from the sensor, information indicative of a position of an index finger of a wearer of the head mounted display, wherein the input to manipulate the position of the instrument comprises movement of the index finger from a first position to a second position.

8. The system of claim 1, wherein the at least one processor is further programmed to:
    transmit, to the server, instructions to adjust the instrument to the second position.

9. The system of claim 1, wherein the at least one processor is further programmed to:
    receive, via an input device, input to manipulate a position of a portion of the subject-specific anatomical model.

10. The system of claim 1, wherein the at least one processor is further programmed to:
    transmit, to the server, instructions to adjust a position of a portion of the subject-specific anatomical model.

11. The system of claim 1, wherein the at least one processor is further programmed to:
    receive, via an input device, input to change a portion of the simulation that is visualized.

12. The system of claim 1, wherein the at least one processor is further programmed to:
    transmit, to the server, instructions to change a portion of the simulation that is visualized.

13. The system of claim 1, wherein the anatomical atlas comprises a brain atlas.

14. A method for presenting biophysical simulations in an interactive mixed reality environment, comprising:
    receiving medical imaging data associated with a subject, the medical imaging data comprising T1-weighted magnetic resonance imaging (MRI) data, T2-weighted MRI data, or computed tomography (CT) data corresponding to the subject's brain tissue;
    receiving, from a server, information useable to visualize a simulation of one or more biophysical processes associated with the subject in connection with a subject-specific anatomical model associated with the subject based on the medical imaging data with an instrument in a first position, wherein the server generates the subject-specific anatomical model based on the medical imaging data by using a nonlinear transformation matrix and a warp field with an anatomical atlas;
    causing a visualization of the simulation to be presented, via a transparent display of a head mounted display device, in connection with the medical imaging data with the instrument presented in the first position;
    receiving, from the server, updated information useable to visualize an updated simulation of the one or more biophysical processes in connection with the subject-specific anatomical model based on the medical imaging data with the instrument in a second position; and
    causing a visualization of the updated simulation to be presented, via the transparent display, in connection with the medical imaging data with the instrument presented in the second position.

15. The method of claim 14, wherein the instrument is a deep brain stimulation (DBS) electrode comprising multiple electrode contacts, a convection enhanced delivery (CED) probe, or a laser interstitial thermal therapy (LITT) probe.

16. The method of claim 14, wherein the anatomical atlas comprises a brain atlas.

17. A non-transitory computer readable medium containing computer executable instructions that, when executed by processing circuitry, cause the processing circuitry to:

receive medical imaging data associated with a subject, the medical imaging data comprising computed tomography (CT) data corresponding to the subject's brain tissue;

receive, from a server, information useable to visualize a simulation of one or more biophysical processes associated with the subject in connection with a subject-specific anatomical model associated with the subject based on the medical imaging data with an instrument in a first position, wherein the server generates the subject-specific anatomical model based on the medical imaging data by using a nonlinear transformation matrix and a warp field with an anatomical atlas;

cause a visualization of the simulation to be presented, via a transparent display of a head mounted display device, in connection with the medical imaging data with the instrument presented in the first position;

receive, from the server, updated information useable to visualize an updated simulation of the one or more biophysical processes in connection with the subject-specific anatomical model based on the medical imaging data with the instrument in a second position; and cause a visualization of the updated simulation to be presented, via the transparent display, in connection with the medical imaging data with the instrument presented in the second position.

18. The non-transitory computer readable medium of claim 17, wherein the medical imaging data comprises T1-weighted magnetic resonance imaging (MRI) data or T2-weighted MRI data corresponding to the subject's brain tissue.

19. The non-transitory computer readable medium of claim 17, wherein the anatomical atlas comprises a brain atlas.

20. The non-transitory computer readable medium of claim 17, wherein the instrument is a deep brain stimulation (DBS) electrode comprising multiple electrode contacts, a convection enhanced delivery (CED) probe, or a laser interstitial thermal therapy (LITT) probe.

* * * * *